United States Patent [19]

Watanabe et al.

[11] Patent Number: 5,750,675

[45] Date of Patent: May 12, 1998

[54] 2'-"UP" FLUORINATED 2'-DEOXY-ARABINOFURANOSYLPURINES

[75] Inventors: Kyoichi A. Watanabe, Rye Brook; Krzysztof W. Pankiewicz; Jacek Krzeminski, both of Bronxville, all of N.Y.; Barbara Nawrot, Zgierz, Poland

[73] Assignee: Sloan-Kettering Institute for Cancer Research, New York, N.Y.

[21] Appl. No.: 470,749

[22] Filed: Jun. 6, 1995

Related U.S. Application Data

[62] Division of Ser. No. 273,771, Jul. 12, 1994, abandoned, which is a continuation of Ser. No. 102,544, Aug. 5, 1993, abandoned, which is a continuation of Ser. No. 997,103, Dec. 24, 1992, abandoned, which is a continuation of Ser. No. 630,275, Dec. 18, 1990, abandoned.

[51] Int. Cl.[6] .................. C07H 19/16; C07H 19/19; C07H 19/167; C07H 19/173

[52] U.S. Cl. .................. 536/27.21; 536/27.4; 536/27.6; 536/27.61; 536/27.62; 536/27.63; 536/27.7; 536/28.8; 536/27.81

[58] Field of Search ................ 536/27.21, 27.6, 536/27.4, 27.61, 27.62, 27.63, 27.7, 27.8, 27.81

[56] References Cited

U.S. PATENT DOCUMENTS

| | | | |
|---|---|---|---|
| 3,687,931 | 8/1972 | Verheyden et al. | 536/27.14 |
| 4,751,221 | 6/1988 | Watanabe et al. | 514/46 |
| 4,918,179 | 4/1990 | Watanabe et al. | 536/27.4 |
| 5,034,518 | 7/1991 | Montgomery et al. | 536/27.4 |
| 5,126,506 | 6/1992 | Sterzycki et al. | 536/27.4 |
| 5,384,310 | 1/1995 | Montgomery et al. | 514/46 |

FOREIGN PATENT DOCUMENTS

| | | |
|---|---|---|
| 0285432 | 10/1988 | European Pat. Off. |
| 0339161 | 11/1989 | European Pat. Off. |
| 0352248 | 1/1990 | European Pat. Off. |
| 0392791 | 10/1990 | European Pat. Off. |
| 0417999 | 3/1991 | European Pat. Off. |
| 8908658 | 9/1989 | WIPO |
| 9014352 | 11/1990 | WIPO |
| 9107180 | 5/1991 | WIPO |
| 9108743 | 6/1991 | WIPO |
| 9110671 | 7/1991 | WIPO |

OTHER PUBLICATIONS

Borthwick et al.(I), "Synthesis and Enzymatic Resolution of Carbocyclic 2'-Ara-Fluoro-Guanosine: A Potent New Anti- Herpetic Agent." *J. Chem. Soc., Chem. Communications*, 1988, 656–658.

Chu et al., "Nucleosides. CXXXV. Synthesis of Some 9-(2-Deoxy-2-fluoro-β-D-arabinofuranosyl)-9-H-purines and Their Biological Activities," *Chem. Pharm. Bull.*, 37(2), 336-339 (1989).

Montgomery et al. (IV), "9-(2-Deoxy-2-fluoro-β-D-arabinofuranosyl)guanine: A Metabolically Stable Cytotoxic Analogue of 2'-Deoxyguanosine," *J. Med. Chem.*, 29(11), 2389–2392 (1986).

Ikehara et al., "Studies on Nucleosides and Nucleotides. LXXXIX. Purine Cyclonucleosides. (43). Synthesis and Properties of 2'-Halogeno-2'-deoxyguanosines." *Chem. Pharm. Bull.*, 29(11), 3281–3285 (1981).

Stoeckler et al., "C(2')-Substituted Purine Nucleoside Analogs," *Biochemical Pharmacology*, 31(9), 1723–1728 (1982).

Uesugi et al., "Synthesis and Properties of ApU Analogues Containing 2'-Halo-2'-deoxyadenosines. Effects of 2'-Substituents on Oligonucleotide Conformation." *Biochemistry*, 21(23), 5870–5877 (1982).

Borthwick et al., (II), "Enantiospecific Synthesis of the Potent Anti-Herpetic Carbocyclic 9-(2'-Deoxy-2'-fluoro-β-D-arabinofuranosyl)guanine (+)C-AFG from Aristeromycin," *Tett. Lett.*, 31(5), 767–770 (1990).

Rainey et al., "Inosine Analogs as Anti-Leishmanial Agents," *Pharmaceutical Research*, 1985(5), 195–252.

Burchenal et al., "Experimental and Clinical Studies on 2'-Fluoroarabinosyl Pyrimidines and Purine-Like C-Nucleosides," in *Nucleosides, Nucleotides, and Their Biological Applications*, Rideout et al. eds., Academic Press, New York, 1982, see pp. 47–65.

(List continued on next page.)

Primary Examiner—John Kight
Assistant Examiner—L. Eric Crane
Attorney, Agent, or Firm—John P. White

[57] ABSTRACT

The present invention provides a compound having the structure:

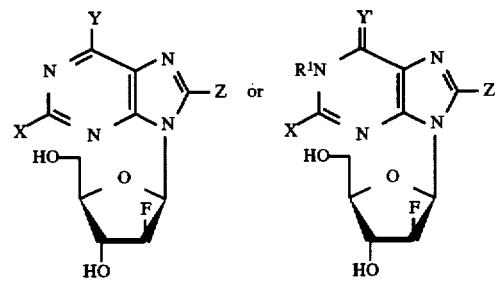

wherein $R^1$ is hydrogen, benzyl or a substituted benzyl group;

X is hydrogen, a flouro, an amino or a substituted amino group;

Y is hydrogen, a methoxy, a methylthio, a benzylthio, a methylethyl, a chloro, an amino or a substituted amino group; and Y' is an oxo or a thio group; and Z is hydrogen, a hydroxy, a methoxy, a halogen, an amino or a substituted amino group.

The present invention also provides a method of synthesizing a compound having the above-identified structure as well as the intermediate compounds produced according to that method.

4 Claims, 1 Drawing Sheet

OTHER PUBLICATIONS

Robins et al., "Selective Modification and Deoxygenation at C2' of Nucleosides." in *Nucleosides, Nucleotides, and Their Biological Applications*, Rideout et al. eds., Academic Press, New York, 1982, see pp. 279–296.

Krzeminski et al., "Synthesis of 9-(2-Deoxy-2-fluoro-β-D-arabinofuranosyl)hypoxanthine. The First Direct Introduction of a 2'-β-Fluoro Substituent in Preformed Purine Nucleosides. Studies Directed Towards the Synthesis of 2'-Deoxy-2'-substituted Arabinonucleosides," *Nucleosides & Nucleotides*, 10(4), 781–798 (1991); *Chem. Abstr.*, 115(19), p. 1071, Abstr. 208436x (1991).

Ikehara et al., "Polynucleotides. LVI. Synthesis and Properties of Poly(2'-Deoxy-2'-Fluoroinosinic Acid)," *Nucleic Acids Res.*, 5(9), 3315–3324 (1978); *Chem. Abstr.*, 90(5), pp. 158–159, Abstr. No. 35123c (1979); only Abstract provided.

Kochetkov et al., *Organic Chemistry of Nucleic Acids, Part B*, Plenum Press, London, UK, 1972, see pp. 450–461.

Middleton, W. (1975) *J. Org. Chem.* New Fluorinating Reagents. Dialkylaminosulfur Fluorides, 40(5) pp. 574–578.

Sharma et al. (1977) *Tetrahedron Letters* A General and Convenient Method for Synthesis of 6-Fluoro-6-Deoxyhexoses, No. 6 pp. 573–576.

Fieser, M. (1977) *Reagents for Organic Synthesis*, vol. 6 pp. 183–184.

Fieser, M. (1986) *Reagents for Organic Synthesis*, vol. 12 pp. 558–559.

Fieser, M. (1986) *Reagents for Organic Synthesis*, vol. 11 p. 590.

Fieser, M. (1982) *Reagents for Organic Synthesis*, vol. 10 pp. 142–143.

Fieser, M. (1982) *Reagents for Organic Synthesis*, vol. 10 pp. 123–125.

Fieser, M. (1982) *Reagents for Organic Synthesis*, vol. 10 pp. 452–453.

Fieser, M. (1980) *Reagents for Organic Synthesis*, vol. 8 pp. 166–167.

Fieser, M. (1986) *Reagents for Organic Synthesis*, vol. 12 pp. 183–184.

Herdewijn et al. (1987) *J. Med. Chem.* Synthesis and Anti-HIV Activity of Various 2'- and 3'-Substituted 2', 3'-Dideoxyadenosines: A Structure-Activity analysis, vol. 30 pp. 2131–2137.

Herdewijn et al. (1989) *Nucleosides & Nucleotides* Synthesis of Nucleosides Fluorinated in the Sugar Moiety. The Application of Diethylaminosulfur Trifluoride to the Synthesis of Fluorinated Nucleosides, vol. 8(1) pp. 65–96.

Marquez et al. (1990) *J. Med. Chem.* Acid–Stable 2'-Fluoro Purine Dideoxynucleosides as Active Agents Against HIV, vol. 33 pp. 978–985.

Montgomery et al. (1992) *J. Med. Chem.* Synthesis and Biologic Activity of 2'-Fluoro-2-halo Derivatives of 9-B-D-Arabinofuranosyladenine, vol. 35 pp. 397–401.

Pankiewicz et al. (1992) *J. Org. Chem.* A Synthesis of 9-(2-Deoxy-2-fluoro-B-D arabinosyl) adenine and Hypoxanthine. An Effect of C3'-Endo Conformational Shift on Reaction Course of 2'-Hydroxyl Group with DAST, vol. 57 pp. 553–559.

2'-"UP" FLUORINATED 2'-DEOXY-ARABINOFURANOSYLPURINES

This application is a divisional of U.S. Ser. No. 08/273,771, filed Jul. 12, 1994, now abandoned, which is a continuation of U.S. Ser. No. 08/102,544, filed Aug. 5, 1993, now abandoned, which is a continuation of U.S. Ser. No. 07/997,103, now abandoned, filed Dec. 24, 1992, which is a continuation of U.S. Ser. No. 07/630,275, now abandoned, filed Dec. 18, 1990.

The invention described herein was made in the course of work under Grant No. CA-78601 from the National Cancer Institute, National Institutes of Health, U. S. Department of Health and Human Services. The U. S. Government may have certain rights in this application.

BACKGROUND OF THE INVENTION

Several purine nucleosides containing a 2'-fluoro-2'-deoxy-β-D-arabinofuranosyl moiety have been synthesized. (Watanabe et al., U.S. Pat. Nos. 4,751,221 and 4,918,179). Several nucleosides which have been synthesized have shown interesting biological activity. Specifically, 9-(2'-fluoro-2'deoxy-β-D-arabinofuranosyl)-hypoxanthine (F-ara-H) has been shown to exhibit inhibitory activity against the pathogenic parasite, Leishmania tropica (Santi et al., Pharm. Res., 1985, 195). The synthetic procedure previously disclosed involved the multi-step preparation of an appropriate carbohydrate derivative which was condensed with 6-chloropurine, and the 6-purine nucleoside product was further converted after several steps into F-ara-H. This synthetic procedure was extremely laborious, time consuming, and the yield of F-ara-H was very low.

This invention discloses a superior method of preparation starting from the readily available preformed nucleosides. There has not previously been known a procedure to introduce a fluorine substituent to the C2' position of a preformed nucleoside. The procedure invented is effective not only for preparation of F-ara-H but also for -2-fluoro-arabinosylpurine nucleosides in general in terms of steps involved, overall time required and yields of the desired nucleoside products.

SUMMARY OF THE INVENTION

The present invention provides a compound having the structure:

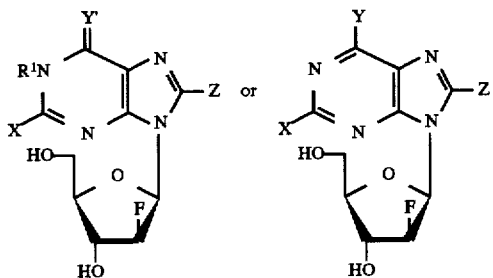

wherein
R$^1$ is hydrogen, benzyl or a substituted benzyl group;
X is hydrogen, a fluoro, an amino or a substituted amino group;
Y is hydrogen, a methoxy, a methylthio, a benzylthio, an isopropyl, a chloro, an amino
Y' is an oxo or a thio group; and
Z is hydrogen, a hydroxy, a methoxy, a halogen, an amino or a substituted amino group.

The present invention also provides a process for synthesizing a compound having the structure:

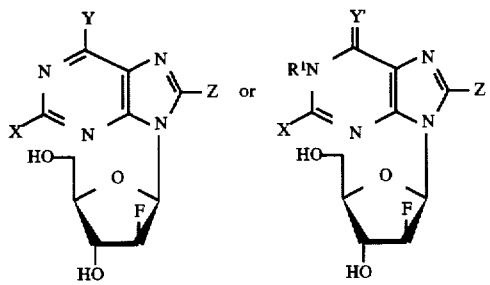

wherein
R$^1$ is hydrogen, benzyl or a substituted benzyl group;
X is hydrogen, a fluoro, an amino or a substituted amino group;
Y is hydrogen, a methoxy, a methylthio, a benzylthio, an isopropyl, a chloro, an amino or a substituted amino group;
Y' is an oxo or a thio group; and
Z is hydrogen, a hydroxy, a methoxy, a halogen, an amino or a substituted amino group;
which comprises:
(a) treating a starting compound having the structure:

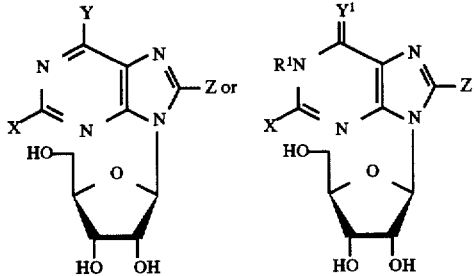

wherein
R$^1$ is hydrogen, benzyl or a substituted benzyl group;
X is hydrogen, a fluoro, an amino or a substituted amino group;
Y is hydrogen, a methoxy, a methylthio, a benzylthio, an isopropyl, a chloro, an amino or a substituted amino group;
Y' is an oxo or a thio group; and
Z is hydrogen, a hydroxy, a methoxy, a halogen, an amino or a substituted amino group;
under such conditions so as to form a compound having the structure:

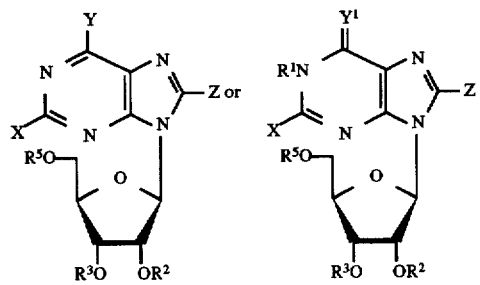

wherein $R^5$ is triphenylmethyl, diphenyl (4-methoxyphenyl) methyl, on phenyldi(4-methoxyphenyl)methyl;

$R^3$ and $R^2$ are either both hydrogen or one of $R^3$ and $R^2$ is hydrogen and the other is triphenylmethyl, diphenyl (4-methoxyphenyl)methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;

$R^1$ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group;

(b) treating the compound formed in step (a) under such conditions so as to form a compound having the structure:

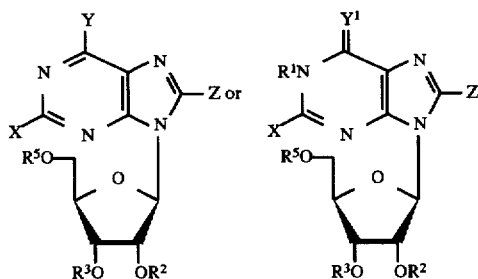

wherein $R^5$ is triphenylmethyl, diphenyl(4-methoxyphenyl) methyl, or phenyldi(4 -methoxyphenyl)methyl;

$R^3$ and $R^2$ are different wherein one of $R^3$ and $R^2$ is triflyl and the other is triphenylmethyl, diphenyl(4-methoxyphenyl)methyl, phenyldi(4-methoxyphenyl) methyl, tetrahydropyranyl, acetyl, propanoyl, benzoyl, anisoyl, toluoyl, nitrobenzoyl, benzyl, toluyl, methoxybenzyl, or nitrobenzyl;

$R^1$ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group;

(c) treating the compound formed in step (b) under such conditions so as to form a compound having the structure:

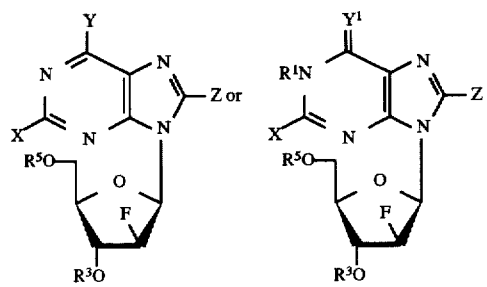

wherein $R^5$ is triphenylmethyl, diphenyl(4-methoxyphenyl) methyl, or phenyldi(4-methoxyphenyl)methyl;

$R^3$ is triphenylmethyl, diphenyl(4-methoxyphenyl) methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;

$R^1$ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group; and (d) treating the compound formed in step (c) under such conditions so as to form a compound having the structure:

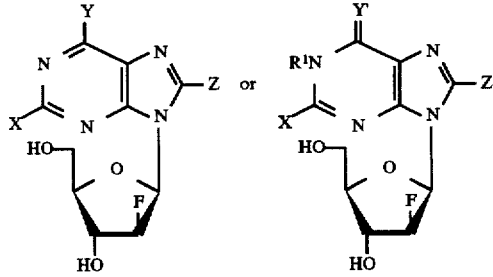

wherein $R^1$ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y is an oxo or a thio group; and

Z is hydrogen, a hydroxy, a methoxy, a halogen, an amino or a substituted amino group;

The present invention also provides a compound having the structure:

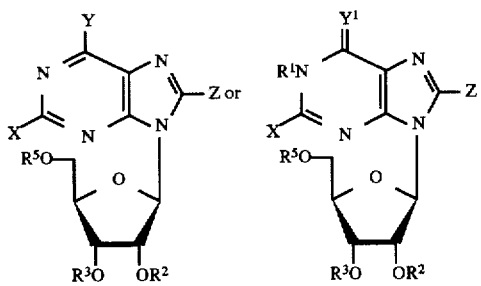

wherein

R⁵ is triphenylmethyl, diphenyl(4-methoxyphenyl) methyl, or phenyldi(4-methoxyphenyl)methyl;

R³ and R² are either the same or different and are hydrogen, triflyl, triphenylmethyl, diphenyl(4-methoxyphenyl)methyl, phenyldi(4-methoxyphenyl) methyl, tetrahydropyranyl, acetyl, propanoyl, benzoyl, anisoyl, toluoyl, nitrobenzoyl, benzyl, toluyl, methoxybenzyl, or nitrobenzyl;

X is hydrogen, a fluoro, an amino or a substituted amino group;

Y is hydrogen, a methoxy, a methylthio, a benzylthio, an isopropyl, a chloro, an amino or a substituted amino group; and Y' is an oxo of a thio group; and Z is hydrogen, a hydroxy, a methoxy, a halogen, an amino or a substituted amino group;

The present invention also provides a compound having the structure:

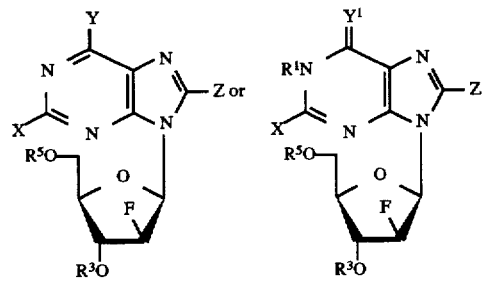

wherein

R⁵ is triphenylmethyl, diphenyl(4-methoxyphenyl) methyl, or phenyldi(4-methoxyphenyl)methyl;

R³ is hydrogen, triflyl, triphenylmethyl, diphenyl(4-methoxyphenyl)methyl, phenyldi(4-methoxyphenyl) methyl, tetrahydropyranyl, acetyl, propanoyl, benzoyl, anisoyl, toluoyl, nitrobenzoyl, benzyl, toluyl, methoxybenzyl, or nitrobenzyl;

R¹ is hydrogen, benzyl or a substituted benzyl group;

X is hydrogen, a fluoro, an amino or a substituted amino;

Y is hydrogen, a methoxy, a methylthio, a benzylthio, a methylethyl, a chloro, an amino or a substituted amino;

Y' is an oxo or a thio group; and

Z is hydrogen, a hydroxy, a methoxy, a halogen, an amino or a substituted amino.

DETAILED DESCRIPTION OF THE INVENTION

Figure 1:
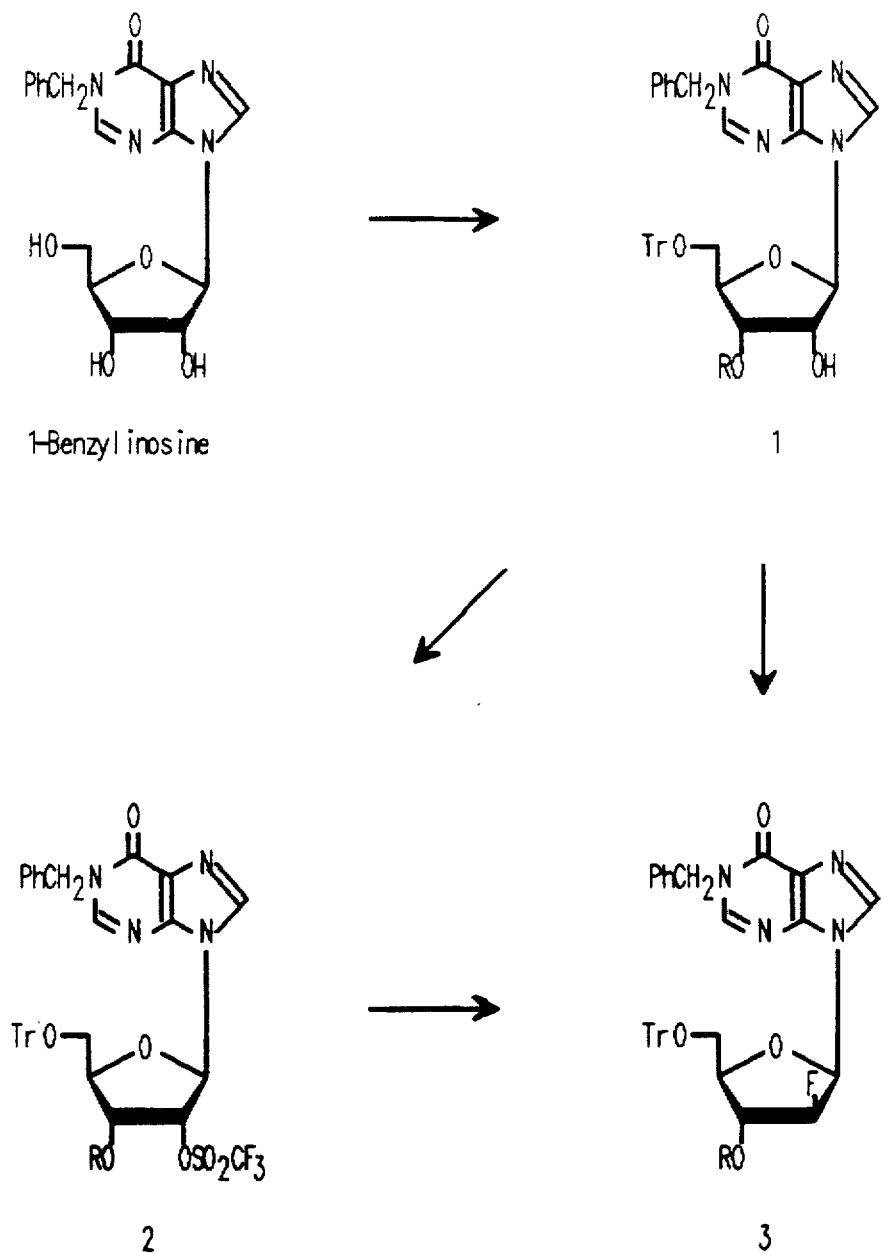
FIG. 1. This figure represents a scheme of two methods of synthesis of 2'-"up" fluorinated nucleosides starting with the preformed nucleoside, 1-benzylinosine. R represents either an acetyl group (a) or a trityl group (b). The 2'-"up" fluorinated nucleosides may be synthesized by either protecting the 3' and 5' positions followed by triflylation and then fluoridation with TASF or directly treating a 3' and 5' trityl-protected nucleoside with DAST.

The present invention provides a compound having the structure:

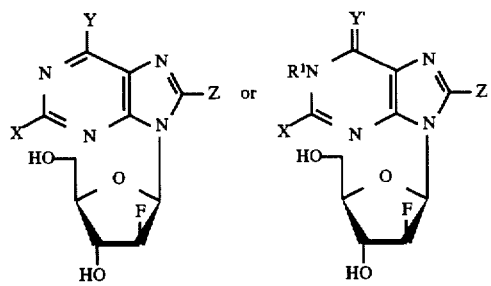

wherein

R¹ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group; and Y' is an oxo or a thio group; and Z is hydrogen, a hydroxy, a methoxy, a halogen, an amino or a substituted amino group.

Compounds having the above-identified structure, although not limited to the following compounds, may be selected from the group consisting of:

9-(2'deoxy-2-fluoro-β-D-arabinofuranosyl)purine, 9-(2'deoxy-2-fluoro-β-D-arabinofuranosyl)-6-chloropurine, 9-(2'deoxy-2-fluoro-β-D-arabinofuranosyl)-6-thiopurine, 9-(2'deoxy-2-fluoro-β-D-arabinofuranosyl)-6-methylthiopurine, 9-(2'deoxy-2-fluoro-β-D-arabinofuranosyl)-6-aminomethylpurine, 9-(2'deoxy-2-fluoro-β-D-arabinofuranosyl)-6-dimethylaminopurine, 9-(2'deoxy-2-fluoro-β-D-arabinofuranosyl)-2-aminopurine, 9-(2'deoxy-2-fluoro-β-D-arabinofuranosyl)-2-acetamidopurine, 9-(2'deoxy-2-fluoro-β-D-arabinofuranosyl)-2-benzamidopurine, 9-(2'deoxy-2-fluoro-β-D-arabinofuranosyl)-2-isobytanamidopurine, 9-(2'deoxy-2-fluoro-β-D-arabinofuranosyl)-2,6-diaminopurine, 9-(2'deoxy-2-fluoro-β-D-arabinofuranosyl)-2,6-diacetamidopurine, 9-(2'deoxy-2-fluoro-β-D-arabinofuranosyl)-2,6-dibenzamidopurine, 9-(2'deoxy-2-fluoro-β-D-arabinofuranosyl)-2,6-diisobutanamidopurine, 9-(2'deoxy-2-fluoro-β-D-arabinofuranosyl)-2-amino-6-chloropurine, 9-(2'deoxy-2-fluoro-β-D-arabinofuranosyl)-2-amino-6-thiopurine, 9-(2'deoxy-2-fluoro-β-D-arabinofuranosyl)-2-amino-6-methylthiopurine, 9-(2'deoxy-2-fluoro-β-D-arabinofuranosyl)-2-fluoropurine, 9-(2'deoxy-2-fluoro-β-D-arabinofuranosyl)-2-fluoro-6-thiopurine, 9-(2'deoxy-2-fluoro-β-D-arabinofuranosyl)-2-fluoro-6-methylthiopurine, 9-(2'deoxy-2-fluoro-β-D-arabinofuranosyl)-2-fluoro-6-aminomethylpurine, 9-(2'deoxy-2-fluoro-β-D-arabinofuranosyl)-2-fluoro-6-dimethylaminopurine, 9-(2'deoxy-2-fluoro-β-D-arabinofuranosyl)adenine, 9-(2'-deoxy-2-fluoro-β-D-arabinofuranosyl)-2-fluoroadenine, 9-(2'-deoxy-2-fluoro-β-D-arabinofuranosyl)-2-acetamidoadenine, 9-(2'-deoxy-2-fluoro-β-D-arabinofuranosyl)-2-benzamidoadenine, 9-(2'-deoxy-2-fluoro-β-D-arabinofuranosyl)-2-isobutanamidoadenine, 9-(2'-deoxy-2-fluoro-β-D-arabinofuranosyl)-$N^6$-trityladenine, 9-(2'-deoxy-2-fluoro-β-D-arabinofuranosyl)-$N^6$-acetyladenine, 9-(2'-deoxy-2-fluoro-β-D-arabinofuranosyl)-$N^6$-benzoyladenine, 9-(2'deoxy-2'-fluoro-β-D-arabinofuranosyl)thioguanine, 9-(2'deoxy-2'-fluoro-β-D-arabinofuranosyl)-2-fluorohypoxanthine, 9-(2'deoxy-2'-fluoro-β-D-arabinofuranosyl)hypoxanthine, or 9-(2'deoxy-2'-fluoro-β-D-arabinofuranosyl)guanine.

The present invention also provides a process for synthesizing a compound having the structure:

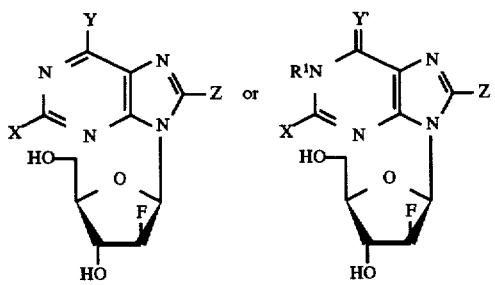

wherein $R^1$ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group;

which comprises:

(a) treating a starting compound having the structure:

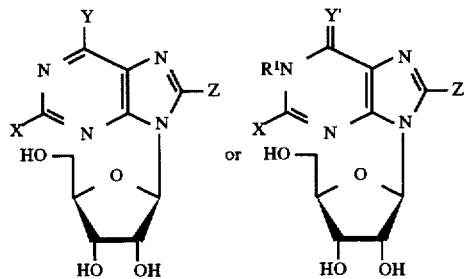

wherein $R^1$ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group;

under such conditions so as to form a compound having the structure:

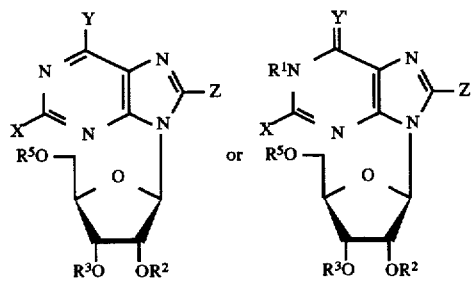

wherein $R^5$ is triphenylmethyl, diphenyl(4-methoxyphenyl)methyl, or phenyldi(4-methoxyphenyl)methyl;

$R^3$ and $R^2$ are either both hydrogen or one of $R^3$ and $R^2$ is hydrogen and the other is triphenylmethyl, diphenyl(4-methoxyphenyl)methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;

$R^1$ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group;

(b) treating the compound formed in step (a) under such conditions so as to form a compound having the structure:

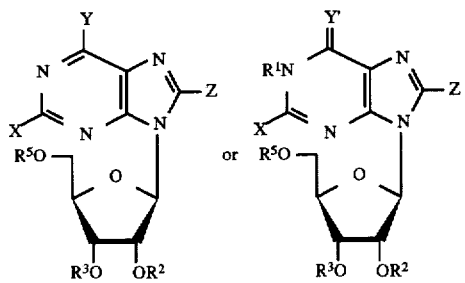
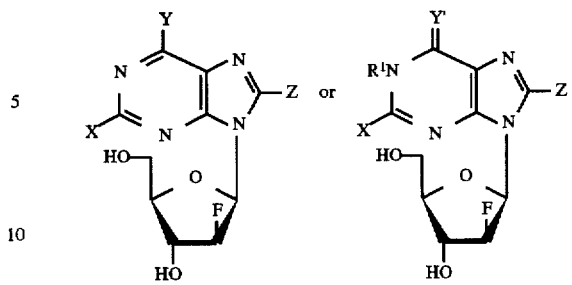

wherein

R⁵ is triphenylmethyl, diphenyl(4-methoxyphenyl)-methyl, or phenyldi(4-methoxyphenyl)methyl;

R³ and R² are different wherein one of R³ and R² is triflyl and the other is triphenylmethyl, diphenyl(4-methoxyphenyl)methyl, phenyldi(4-methoxyphenyl) methyl, tetrahydropyranyl, acetyl, propanoyl, benzoyl, anisoyl, toluoyl, nitrobenzoyl, benzyl, toluyl, methoxybenzyl, or nitrobenzyl;

R¹ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group;

(c) treating the compound formed in step (b) under such conditions so as to form a compound having the structure:

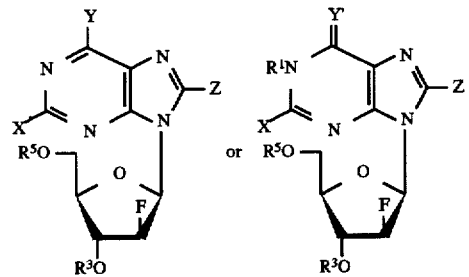

wherein

R⁵ is triphenylmethyl, diphenyl(4-methoxyphenyl) methyl, or phenyldi(4-methoxyphenyl)methyl;

R³ is triphenylmethyl, diphenyl(4-methoxyphenyl) methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;

R¹ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group; and (d) treating the compound formed in step (c) under such conditions so as to form a compound having the structure:

wherein

R¹ is hydrogen, benzyl or a substituted benzyl group;

X is hydrogen, a fluoro, an amino or a substituted amino group;

Y is hydrogen, a methoxy, a methylthio, a benzylthio, an isopropyl, a chloro, an amino or a substituted amino group;

Y' is an oxo or a thio group; and

Z is hydrogen, a hydroxy, a methoxy, a halogen, an amino or a substituted amino group;

In one embodiment of the present invention, the treating in step (a) comprises contacting the starting compound of step (a) with a suitable amount of trityl chloride or a related protecting group in the presence of an organic solvent. ("trityl" as used herein is triphenylmethyl). The treating is performed at room temperature for an effective amount of time to promote reaction. The suitable amount of trityl chloride is enough trityl chloride to promote reaction. The preferred organic solvent is pyridine.

In another embodiment, the treating in step (a) comprises contacting the compound of step (a) with a strong organic base and a suitable amount of trityl cloride or a related protecting group in an organic solvent. In the preferred embodiment, the treating is performed at a temperature range of 70° to 80° C. The strong organic base is preferably 4-dimethylaminopyridine. The preferred organic solvent is pyridine. The suitable amount of trityl chloride is enough trityl chloride to promote reaction.

The treating in step (a) is not limited to contacting the starting compound of step (a) with trityl chloride. The treating may also comprise contacting the starting compound of step (a) with other protecting groups such as diphenyl(4-methoxyphenyl)methyl, phenyldi(4-methoxyphenyl)methyl, tetahydropyranyl acetyl, propanoyl, benzoyl, anisoyl, toluoyl, nitrobenzoyl, benzyl, toluyl, methoxybenzyl, or nitrobenzyl.

In one embodiment, the treating in step (b) comprises contacting the compound formed in step (a) with dibutylin oxide under heat to form a residue, contacting the residue so formed with a suitable amount of triflyl chloride or a related triflylating agent to form a solution, and treating the solution so formed with acetic anhydride. The suitable amount of triflyl chloride is enough triflyl chloride to promote reaction. ("triflyl" as used herein is trifluoromethyl-sulfonyl).

In another embodiment, the treating in step (b) comprises contacting the compound formed in step (a) with 4-dimethylaminopyridine, triethylamine in methylene chloride and a suitable amount of triflyl chloride or a related triflylating agent. The suitable amount of triflyl chloride is enough triflyl chloride to promote reaction.

The treating in step (c) comprises contacting the compound formed in step (b) with a suitable amount of a fluorinating agent. The fluorinating agent may be but is not limited to the following: potassium fluoride in dimethylformamide, tetrabutyl ammonium fluoride in dimethylformamide, Amberlyst 26 (F⁻ form) in acetone, or tris(dimethylamino)-sulfur(trimethylsilyl)-difluoride (TASF) in methylene chloride. In the above process, the preferred fluorinating agent is tris(dimethyamino)-sulfur-(trimethylsilyl)difluoride (TASF) in methylene chloride. The suitable amount of the fluorination agent is enough fluorinating agent to promote reaction. The treating is preferably performed in an argon atmosphere at a temperature of about –70° C.

The treating in step (d) comprises contacting the compound formed in step (c) with a suitable amount of an acid. The preferable acid is trifluoracetic acid. The treating is preferably performed in an argon atmosphere at a temperature of about –25° C. The suitable amount of acid is enough acid to promote reaction.

The present invention also provides another process for synthesizing the compound above which comprises (a) treating a starting compound having the structure:

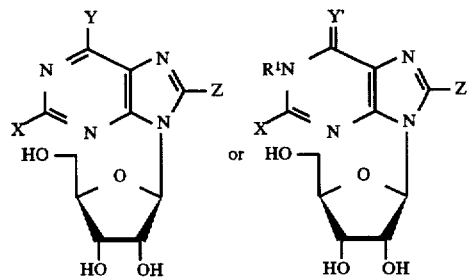

wherein
R¹ is hydrogen, benzyl or a substituted benzyl group;
X is hydrogen, a fluoro, an amino or a substituted amino group;
Y is hydrogen, a methoxy, a methylthio, a benzylthio, an isopropyl, a chloro, an amino or a substituted amino group;
Y' is an oxo or a thio group; and
Z is hydrogen, a hydroxy, a methoxy, a halogen, an amino or a substituted amino group;
under such conditions so as to form a compound having the structure:

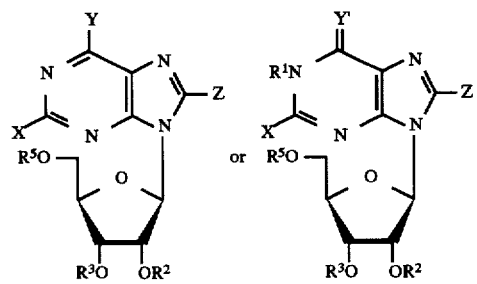

wherein
R⁵ is triphenylmethyl, diphenyl(4-methoxyphenyl)methyl, or phenyldi(4-methoxyphenyl)methyl;
R³ and R² are different, wherein one of R³ and R² is hydrogen and the other is triphenylmethyl, diphenyl(4-methoxyphenyl)methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;
R¹ is hydrogen, benzyl or a substituted benzyl group;

X is hydrogen, a fluoro, an amino or a substituted amino group;
Y is hydrogen, a methoxy, a methylthio, a benzylthio, a methylethyl, a chloro, an amino or a substituted amino group;
Y' is an oxo or a thio group; and
Z is hydrogen, a hydroxy, a methoxy, a halogen, an amino or a substituted amino group;

(b) treating the compound formed in step (a) under such conditions so as to form a compound having the structure:

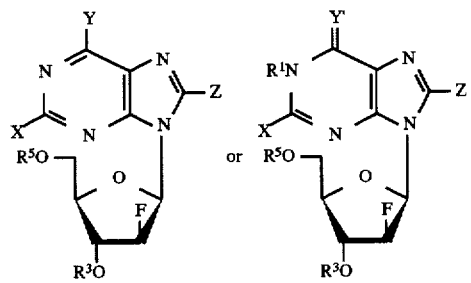

wherein
R⁵ is triphenylmethyl, diphenyl(4-methoxyphenyl)methyl, or phenyldi(4-methoxyphenyl)methyl;
R³ is triphenylmethyl, diphenyl(4-methoxyphenyl)methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;
R¹ is hydrogen, benzyl or a substituted benzyl group;
X is hydrogen, a fluoro, an amino or a substituted amino group;
Y is hydrogen, a methoxy, a methylthio, a benzylthio, an isopropyl, a chloro, an amino or a substituted amino group;
Y' is an oxo or a thio group; and
Z is hydrogen, a hydroxy, a methoxy, a halogen, an amino or a substituted amino group; and (c) treating the compound formed in step (b) under such conditions so as to form a compound having the structure:

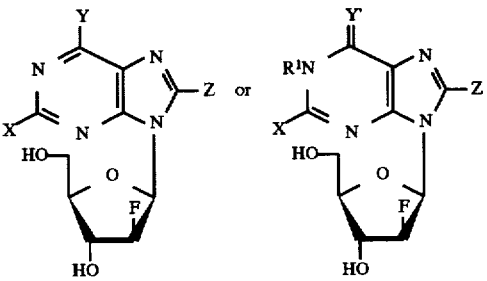

wherein
R¹ is hydrogen, benzyl or a substituted benzyl;
X is hydrogen, a fluoro, an amino or a substituted amino group;
Y is hydrogen, a methoxy, a methylthio, a benzylthio, an isopropyl, a chloro, an amino or a substituted amino group;
Y' is an oxo or a thio group; and
Z is hydrogen, a hydroxy, a methoxy, a halogen, an amino or a substituted amino group;

The above process is the preferred process of synthesis.

The treating in step (a) comprises contacting the starting compound of step (a) with a strong organic base and a suitable amount of trityl cloride or a substitute derivative thereof in an organic solvent. The treating is preferable performed at a temperature range of 70° to 80° C. The strong organic base is preferably 4-dimethylaminopyridine and the organic solvent is preferably pyridine. The suitable amount of trityl chloride is enough trityl chloride to promote reaction.

The treating in step (b) comprises contacting the compound formed in step (a) with a suitable amount of diethylaminosulfurtrifluoride (DAST) or a related fluorinating agent. The treating is best performed at a temperature below −50° C. The suitable amount of diethylaminosulfurtrifluoride (DAST) is enough diethylaminosulfurtrifluoride (DAST) to promote reaction.

The treating in step (c) comprises contacting the compound formed in step (b) with a suitable amount of an acid. The acid is preferably trifuoracetic acid. The suitable amount of the acid is enough acid to promote reaction. The treating is preferably performed in an argon atmosphere at a temperature of about −25° C.

The present invention also provides a compound having the structure:

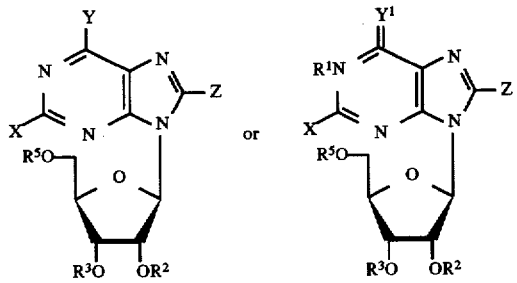

wherein $R^5$ is triphenylmethyl, diphenyl(4-methoxyphenyl)methyl, or phenyldi(4-methoxyphenyl)methyl;

$R^3$ and $R^2$ are either the same or different and are hydrogen, triflyl, triphenylmethyl, diphenyl(4-methoxyphenyl)methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;

X is hydrogen, a fluoro, an amino or a substituted amino group;

Y is hydrogen, a methoxy, a methylthio, a benzylthio, an isopropyl, a chloro, an amino or a substituted amino group; and Y' is an oxo of a thio group; and Z is hydrogen, a hydroxy, a methoxy, a halogen, an amino or a substituted amino group;

Compounds having the above-identified structure, although not limited to the following compounds, may be selected from the group consisting of:

9-(5'-O-trityl-β-D-ribofuranosyl)purine.
9-(5'-O-trityl-β-D-ribofuranosyl)-6-chloropurine.
9-(5'-O-trityl-β-D-ribofuranosyl)-6-aminomethylpurine.
9-(5'-O-trityl-β-D-ribofuranosyl)-2-aminopurine.
9-(5'-O-trityl-β-D-ribofuranosyl)-2-acetamidopurine.
9-(5'-O-trityl-β-D-ribofuranosyl)-2-benzamidopurine.
9-(5'-O-trityl-β-D-ribofuranosyl)-2-isobutanamidopurine.
9-(5'-O-trityl-β-D-ribofuranosyl)-2,6-diaminopurine.
9-(5'-O-trityl-β-D-ribofuranosyl)-2,6-diacetamidopurine.
9-(5'-O-trityl-β-D-ribofuranosyl)-2,6-diabenzamidopurine.
9-(5'-O-trityl-β-D-ribofuranosyl)-2,6-diisobutanmidopurine.
9-(5'-O-trityl-β-D-ribofuranosyl)-2-amino-6-chloropurine.
9-(5'-O-trityl-β-D-ribofuranosyl)-2-amino-6-thiopurine.
9-(5'-O-trityl-β-D-ribofuranosyl)-2-amino-6-aminomethylthiopurine.
9-(5'-O-trityl-β-D-ribofuranosyl)-2-fluoropurine.
9-(5'-O-trityl-β-D-ribofuranosyl)-2-fluoro-6-thiopurine.
9-(5'-O-trityl-β-D-ribofuranosyl)-2-fluoro-6-methylthiopurine.
9-(5'-O-trityl-β-D-ribofuranosyl)-2-fluoro-6-dimethylaminopurine.
9-(5'-O-trityl-β-D-ribofuranosyl)-2-fluoroadenine.
9-(3'-O-acetyl-2'-O-triflyl-5'-O-trityl-β-D-ribofuranosyl)purine.
9-(3'-O-acetyl-2'-O-triflyl-5'-O-trityl-β-D-ribofuranosyl)-6-chloropurine.
9-(3'-O-acetyl-2'-O-triflyl-5'-O-trityl-β-D-ribofuranosyl)-6-thiopurine.
9-(3'-O-acetyl-2'-O-triflyl-5'-O-trityl-β-D-ribofuranosyl)-6-methylthiopurine.
9-(3'-O-acetyl-2'-O-triflyl-5'-O-trityl-β-D-ribofuranosyl)-6-aminomethylpurine.
9-(3'-O-acetyl-2'-O-triflyl-5'-O-trityl-β-D-ribofuranosyl)-6-dimethylaminopurine.
9-(3'-O-acetyl-2'-O-triflyl-5'-O-trityl-β-D-ribofuranosyl)-2-aminopurine.
9-(3'-O-acetyl-2'-O-triflyl-5'-O-trityl-β-D-ribofuranosyl)-2-acetamidopurine.
9-(3'-O-acetyl-2'-O-triflyl-5'-O-trityl-β-D-ribofuranosyl)-2-benzamidopurine.
9-(3'-O-acetyl-2'-O-triflyl-5'-O-trityl-β-D-ribofuranosyl)-2-isobutanaidopurine.
9-(3'-O-acetyl-2'-O-triflyl-5'-O-trityl-β-D-ribofuranosyl)-2,6-diaminopurine.
9-(3'-O-acetyl-2'-O-triflyl-5'-O-trityl-β-D-ribofuranosyl)-2,6-diacetamidopurine.
9-(3'-O-acetyl-2'-O-triflyl-5'-O-trityl-β-D-ribofuranosyl)-2,6-dibenzamidopurine.
9-(3'-O-acetyl-2'-O-triflyl-5'-O-trityl-β-D-ribofuranosyl)-2,6-diisobutanamidopurine.
9-(3'-O-acetyl-2'-O-triflyl-5'-O-trityl-β-D-ribofuranosyl)-2-amino-6-chloropurine.
9-(3'-O-acetyl-2'-O-triflyl-5'-O-trityl-β-D-ribofuranosyl)-2-amino-6-thiopurine.
9-(3'-O-acetyl-2'-O-triflyl-5'-O-trityl-β-D-ribofuranosyl)-2-amino-6-methylthiopurine.
9-(3'-O-acetyl-2'-O-triflyl-5'-O-trityl-β-D-ribofuranosyl)-2-fluoropurine.
9-(3'-O-acetyl-2'-O-triflyl-5'-O-trityl-β-D-ribofuranosyl)-2-fluoro-6-thiopurine.
9-(3'-O-acetyl-2'-O-triflyl-5'-O-trityl-β-D-ribofuranosyl)-2-fluoro-6-methylthiopurine.
9-(3'-O-acetyl-2'-O-triflyl-5'-O-trityl-β-D-ribofuranosyl)-2-fluoro-6-aminomethylpurine.
9-(3'-O-acetyl-2'-O-triflyl-5'-O-trityl-β-D-ribofuranosyl)-2-fluoro-6-dimethylaminopurine.
9-(3'-O-acetyl-2'-O-trifyl-5'-O-trityl-β-D-ribofuranosyl)-N-acetyladenine.
9-(3'-O-acetyl-2'-O-triflyl-5'-O-trityl-β-D-ribofuranosyl)-N-benzoyladenine.
9-(3'-O-acetyl-2'-O-triflyl-5'-O-trityl-β-D-ribofuranosyl)-$N^6$-trityladenine.
9-(3'-O-acetyl-2'-O-triflyl-5'-O-trityl-β-D-ribofuranosyl)-2-fluoroadenine.
9-(2',5'-di-O-trityl-β-D-ribofuranosyl)purine.
9-(2',5'-di-O-trityl-β-D-ribofuranosyl)-6-thiopurine.

9-(2',5'-di-O-trityl-β-D-ribofuranosyl)-6-methylthiopurine.
9-(2',5'-di-O-trityl-β-D-ribofuranosyl)-6-aminomethylpurine.
9-(2',5'-di-O-trityl-β-D-ribofuranosyl)-6-dimethylaminopurine.
9-(2',5'-di-O-trityl-β-D-ribofuranosyl)-2-aminopurine.
9-(2',5'-di-O-trityl-β-D-ribofuranosyl)-2-acetamidopurine
9-(2',5'-di-O-trityl-β-D-ribofuranosyl)-2-benzamidopurine
9-(2',5'-di-O-trityl-β-D-ribofuranosyl)-2-isobutanamidopurine
9-(2',5'-di-O-trityl-β-D-ribofuranosyl)-2,6-diaminopurine.
9-(2',5'-di-O-trityl-β-D-ribofuranosyl)-2,6-diacetamidopurine.
9-(2',5'-di-O-trityl-β-D-ribofuranosyl)-2,6-dibenzamidopurine.
9-(2',5'-di-O-trityl-β-D-ribofuranosyl)-2,6-diisobutanamidopurine.
9-(2',5'-di-O-trityl-β-D-ribofuranosyl)-2-amino-6-chloropurine.
9-(2',5'-di-O-trityl-β-D-ribofuranosyl)-2-amino-6-thiopurine.
9-(2',5'-di-O-trityl-β-D-ribofuranosyl)-2-amino-6-methylthiopurine.
9-(2',5'-di-O-trityl-β-D-ribofuranosyl)-2-fluoropurine.
9-(2',5'-di-O-trityl-β-D-ribofuranosyl)-2-fluoro-6-thiopurine.
9-(2',5'-di-O-trityl-β-D-ribofuranosyl)-2-fluoro-6-methylthiopurine.
9-(2',5'-di-O-trityl-β-D-ribofuranosyl)-2-fluoro-6-aminomethylpurine.
9-(2',5'-di-O-trityl-β-D-ribofuranosyl)-2-fluoro-6-dimethylaminopurine.
9-(2',5'-di-O-trityl-β-D-ribofuranosyl)-N$^6$-triyladenine.
9-(2',5'-di-O-trityl-β-D-ribofuranosyl)-N$^6$-acetyladenine.
9-(2',5'-di-O-trityl-β-D-ribofuranosyl)-N$^6$-benzoyladenine.
9-(2',5'-di-O-trityl-β-D-ribofuranosyl)-2-fluoroadenine.
9-(3',5'-di-O-trityl-β-D-ribofuranosyl)purine.
9-(3',5'-di-O-trityl-β-D-ribofuranosyl)-6-chloropurine.
9-(3',5'-di-O-trityl-β-D-ribofuranosyl)-6-thiopurine.
9-(3',5'-di-O-trityl-β-D-ribofuranosyl)-6-methylthiopurine.
9-(3',5'-di-O-trityl-β-D-ribofuranosyl)-6-aminomethylpurine.
9-(3',5'-di-O-trityl-β-D-ribofuranosyl)-6-dimethylaminopurine.
9-(3',5'-di-O-trityl-β-D-ribofuranosyl)-2-aminopurine.
9-(3',5'-di-O-trityl-β-D-ribofuranosyl)-2-acetamidopurine.
9-(3',5'-di-O-trityl-β-D-ribofuranosyl)-2-benzamidopurine.
9-(3',5'-di-O-trityl-β-D-ribofuranosyl)-2-isobutanamidopurine.
9-(3',5'-di-O-trityl-β-D-ribofuranosyl)-2,6-diaminopurine.
9-(3',5'-di-O-trityl-β-D-ribofuranosyl)-2,6-dibenzamidopurine.
9-(3',5'-di-O-trityl-β-D-ribofuranosyl)-2,6-diisobutanamidopurine.
9-(3',5'-di-O-trityl-β-D-ribofuranosyl)-2-amino-6-chloropurine.
9-(3',5'-di-O-trityl-β-D-ribofuranosyl)-2-amino-6-thiopurine.
9-(3',5'-di-O-trityl-β-D-ribofuranosyl)-2-amino-6-methylthiopurine.
9-(3',5'-di-O-trityl-β-D-ribofuranosyl)-2-fluoropurine.
9-(3',5'-di-O-trityl-β-D-ribofuranosyl)-2-fluoro-6-thiopurine.
9-(3',5'-di-O-trityl-β-D-ribofuranosyl)-2-fluoro-6-methylthiopurine.
9-(3',5'-di-O-trityl-β-D-ribofuranosyl)-2-fluoro-6-aminomethylpurine.
9-(3',5'-di-O-trityl-β-D-ribofuranosyl)-2-fluoro-6-dimethylaminopurine.
9-(3',5'-di-O-trityl-β-D-ribofuranosyl)-N$^6$-trityladenine.
9-(3',5'-di-O-trityl-β-D-ribofuranosyl)-N$^6$-acetyladenine.
9-(3',5'-di-O-trityl-β-D-ribofuranosyl)-N$^6$-benzoyladenine.
9-(3',5'-di-O-trityl-β-D-ribofuranosyl)-N$^2$-trityladenine.
9-(3',5'-di-O-trityl-β-D-ribofuranosyl)-N$^2$-acetyladenine.
9-(3',5'-di-O-trityl-β-D-ribofuranosyl)-N$^2$-benzoyladenine.
9-(3',5'-di-O-trityl-β-D-ribofuranosyl)-2-fluoroadenine.
9-(2'-O-triflyl-3',5'-di-O-trityl-β-D-ribofuranosyl)-N$^2$-trityl-6-thiopurine.
9-(2'-O-triflyl-3',5'-di-O-trityl-β-D-ribofuranosyl)purine.
9-(2'-O-triflyl-3',5'-di-O-trityl-β-D-ribofuranosyl)-6-chloropurine.
9-(2'-O-triflyl-3',5'-di-O-trityl-β-D-ribofuranosyl)-6-thiopurine.
9-(2'-O-triflyl-3',5'-di-O-trityl-β-D-ribofuranosyl)-6-methylthiopurine.
9-(2'-O-triflyl-3',5'-di-O-trityl-β-D-ribofuranosyl)-6-aminomethylpurine.
9-(2'-O-triflyl-3',5'-di-O-trityl-β-D-ribofuranosyl)-6-dimethylaminopurine.
9-(2'-O-triflyl-3',5'-di-O-trityl-β-D-ribofuranosyl)-6-aminopurine.
9-(2'-O-triflyl-3',5'-di-O-trityl-β-D-ribofuranosyl)-2-acetamidopurine.
9-(2'-O-triflyl-3',5'-di-O-trityl-β-D-ribofuranosyl)-2-benzamidopurine.
9-(2'-O-triflyl-3',5'-di-O-trityl-β-D-ribofuranosyl)-2-isobutanamidopurine.
9-(2'-O-triflyl-3',5'-di-O-trityl-β-D-ribofuranosyl)-2,6-diaminopurine.
9-(2'-O-triflyl-3',5'-di-O-trityl-β-D-ribofuranosyl)-2,6-diacetamidopurine.
9-(2'-O-triflyl-3',5'-di-O-trityl-β-D-ribofuranosyl)-2,6-dibenzamidopurine.
9-(2'-O-triflyl-3',5'-di-O-trityl-β-D-ribofuranosyl)-2,6-diisobutanamidopurine.
9-(2'-O-triflyl-3',5'-di-O-trityl-β-D-ribofuranosyl)-2-amino-6-chloropurine.
9-(2'-O-triflyl-3',5'-di-O-trityl-β-D-ribofuranosyl)-2-amino-6-thiopurine.
9-(2'-O-triflyl-3',5'-di-O-trityl-β-D-ribofuranosyl)-2-amino-6-methylthiopurine.
9-(2'-O-triflyl-3',5'-di-O-trityl-β-D-ribofuranosyl)-2-fluoropurine.
9-(2'-O-triflyl-3',5'-di-O-trityl-β-D-ribofuranosyl)-2-fluoro-6-thiopurine.
9-(2'-O-triflyl-3',5'-di-O-trityl-β-D-ribofuranosyl)-2-fluoro-6-methylthiopurine.
9-(2'-O-triflyl-3',5'-di-O-trityl-β-D-ribofuranosyl)-2-fluoro-6-aminomethylpurine.
9-(2'-O-triflyl-3',5'-di-O-trityl-β-D-ribofuranosyl)-2-fluoro-6-dimethylaminopurine.
9-(2'-O-triflyl-3',5'-di-O-trityl-β-D-ribofuranosyl)-N$^6$-trityladenine.
9-(2'-O-triflyl-3',5'-di-O-trityl-β-D-ribofuranosyl)-N$^6$-acetyladenine.
9-(2'-O-triflyl-3',5'-di-O-trityl-β-D-ribofuranosyl)-N$^6$-benzoyladenine.
9-(2'-O-triflyl-3',5'-di-O-trityl-β-D-ribofuranosyl)-2-fluoroadenine.
9-(3'-O-triflyl-2',5'-di-O-trityl-β-D-ribofuranosyl)purine.
9-(3'-O-triflyl-2',5'-di-O-trityl-β-D-ribofuranosyl)-6-chloropurine.
9-(3'-O-triflyl-2',5'-di-O-trityl-β-D-ribofuranosyl)-6-thiopurine.

9-(3'-O-triflyl-2',5'-di-O-trityl-β-D-ribofuranosyl)-6-methylthiopurine,
9-(3'-O-triflyl-2',5'-di-O-trityl-β-D-ribofuranosyl)-6-aminomethylpurine,
9-(3'-O-triflyl-2',5'-di-O-trityl-β-D-ribofuranosyl)-6-dimethylaminopurine,
9-(3'-O-triflyl-2',5'-di-O-trityl-β-D-ribofuranosyl)-6-aminopurine,
9-(3'-O-triflyl-2',5-di-O-trityl-β-D-ribofuranosyl)-6-diaminopurine,
9-(3'-O-triflyl-2',5'-di-O-trityl-β-D-ribofuranosyl)-2-amino-6-chloropurine,
9-(3'-O-triflyl-2',5'-di-O-trityl-β-D-ribofuranosyl)-2-amino-6-thiopurine,
9-(3'-O-triflyl-2',5'-di-O-trityl-β-D-ribofuranosyl)-2-amino-6-methylthiopurine,
9-(3'-O-triflyl-2',5'-di-O-trityl-β-D-ribofuranosyl)-2-fluoropurine,
9-(3'-O-triflyl-2',5'-di-O-trityl-β-D-ribofuranosyl)-2-fluoro-6-thiopurine,
9-(3'-O-triflyl-2',5'-di-O-trityl-β-D-ribofuranosyl)-2-fluoro-6-methylthiopurine,
9-(3'-O-triflyl-2',5'-di-O-trityl-β-D-ribofuranosyl)-2-fluoro-6-aminomethylpurine,
9-(3'-O-triflyl-2',5'-di-O-trityl-β-D-ribofuranosyl)-2-fluoro-6-dimethylaminopurine,
9-(3'-O-triflyl-2',5'-di-O-trityl-β-D-ribofuranosyl)-$N^6$-trityladenine,
9-(3'-O-triflyl-2',5'-di-O-trityl-β-D-ribofuranosyl)-$N^6$-acetyladenine,
9-(3'-O-triflyl-2',5'-di-O-trityl-β-D-ribofuranosyl)-$N^6$-benzoyladenine,
9-(3'-O-triflyl-2',5'-di-O-trityl-β-D-ribofuranosyl)-2-fluoroadenine,
9-(5'-O-trityl-β-D-ribofuranosyl)-1-benzylhypoxanthine,
9-(5'-O-trityl-β-D-ribofuranosyl)-2-fluorohypoxanthine,
9-(3'-O-acetyl-2'-O-triflyl-5'-O-trityl-β-D-ribofuranosyl)-1-benzylhypoxanthine,
9-(3'-O-acetyl-2'-O-triflyl-5'-O-trityl-β-D-ribofuranosyl)-2-acetamidoguanine,
9-(3'-O-acetyl-2'-O-triflyl-5'-O-trityl-β-D-ribofuranosyl)-2-benzamidoguanine,
9-(3'-O-acetyl-2'-O-triflyl-5'-O-trityl-β-D-ribofuranosyl)-2-isobutanamidoguanine,
9-(3'-O-acetyl-2'-O-triflyl-5'-O-trityl-β-D-ribofuranosyl)-2-acetamido-6-thioguanine,
9-(3'-O-acetyl-2'-O-triflyl-5'-O-trityl-β-D-ribofuranosyl)-2-benzamido-6-thioguanine,
9-(3'-O-acetyl-2'-O-triflyl-5'-O-trityl-β-D-ribofuranosyl)-2-isobutanamido-6-thioguanine,
9-(3'-O-acetyl-2'-O-triflyl-5'-O-trityl-β-D-ribofuranosyl)-2-fluorohypoxanthine,
9-(2',5'-di-O-trityl-β-D-ribofuranosyl)-hypoxanthine,
9-(2',5'-di-O-trityl-β-D-ribofuranosyl)-1-benzylhypoxanthine,
9-(2',5'-di-O-trityl-β-D-ribofuranosyl)-$N^2$-tritylguanine,
9-(2',5'-di-O-trityl-β-D-ribofuranosyl)-$N^2$-acetylguanine,
9-(2',5'-di-O-trityl-β-D-ribofuranosyl)-$N^2$-benzoylguanine,
9-(2',5'-di-O-trityl-β-D-ribofuranosyl)-$N^2$-isobutyrylguanine,
9-(2',5'-di-O-trityl-β-D-ribofuranosyl)-2-fluorohypoxanthine,
9-(3',5'-di-O-trityl-β-D-ribofuranosyl)-hypoxanthine,
9-(3',5'-di-O-trityl-β-D-ribofuranosyl)-1-benzylhypoxanthine,
9-(3',5'-di-O-trityl-β-D-ribofuranosyl)-$N^2$-isobutyrylguanine,
9-(3',5'-di-O-trityl-β-D-ribofuranosyl)-2-fluorohypoxanthine,
9-(2'-O-trityl-3',5'-di-O-trityl-β-D-ribofuranosyl) hypoxanthine,
9-(2'-O-triflyl-3',5'-di-O-trityl-β-D-ribofuranosyl)-1-benzylhypoxanthine,
9-(2'-O-triflyl-3',5'-di-O-trityl-β-D-ribofuranosyl)-2-fluorohypoxanthine,
9-(2'-O-triflyl-3',5'-di-O-trityl-β-D-ribofuranosyl)-6-thiohypoxanthine,
9-(2'-O-triflyl-3',5'-di-O-trityl-β-D-ribofuranosyl)-$N^6$-tritylguanine,
9-(2'-O-triflyl-3',5'-di-O-trityl-β-D-ribofuranosyl)-$N^2$-acetylguanine,
9-(2'-O-triflyl-3',5'-di-O-trityl-β-D-ribofuranosyl)-$N^2$-benzoylguanine,
9-(2'-O-triflyl-3',5'-di-O-trityl-β-D-ribofuranosyl)-$N^2$-isobutyrylguanine,
9-(2'-O-triflyl-3',5'-di-O-trityl-β-D-ribofuranosyl)-6-thio-$N^2$-acetylguanine,
9-(2'-O-triflyl-3',5'-di-O-trityl-β-D-ribofuranosyl)-6-thio-$N^2$-benzoylguanine,
9-(2'-O-triflyl-3',5'-di-O-trityl-β-D-ribofuranosyl)-6-thio-$N^2$-isobutyrylguanine,
9-(2'-O-triflyl-3',5'-di-O-trityl-β-D-ribofuranosyl)-2-fluorohypoxanthine,
9-(3'-O-triflyl-2',5'-di-O-trityl-β-D-ribofuranosyl) hypoxanthine,
9-(3'-O-triflyl-2',5'-di-O-trityl-β-D-ribofuranosyl)-1-benzyl-hypoxanthine,
9-(3'-O-triflyl-2',5'-di-O-trityl-β-D-ribofuranosyl)-2-fluoro-hypoxanthine,
9-(3'-O-triflyl-2',5'-di-O-trityl-β-D-ribofuranosyl)-6-thio-hypoxanthine,
9-(3'-O-triflyl-2',5'-di-O-trityl-β-D-ribofuranosyl)-$N^2$-tritylguanine,
9-(3'-O-triflyl-2',5'-di-O-trityl-β-D-ribofuranosyl)-$N^2$-acetylguanine,
9-(3'-O-triflyl-2',5'-di-O-trityl-β-D-ribofuranosyl)-$N^2$-benzoylguanine,
9-(3'-O-triflyl-2',5'-di-O-trityl-β-D-ribofuranosyl)-$N^2$-isobutyrylguanine,
9-(3'-O-triflyl-2',5'-di-O-trityl-β-D-ribofuranosyl)-$N^2$-trityl-6-thioguanine,
9-(3'-O-triflyl-2',5'-di-O-trityl-β-D-ribofuranosyl)-6-thio-$N^2$-acetylguanine,
9-(3'-O-triflyl-2',5'-di-O-trityl-β-D-ribofuranosyl)-6-thio-$N^2$-benzoylguanine,
9-(3'-O-triflyl-2',5'-di-O-trityl-β-D-ribofuranosyl)-6-thio-$N^2$-isobutyrlguanine, or
9-(3'-O-triflyl-2',5'-di-O-trityl-β-D-ribofuranosyl)-2-fluorohypoxanthine.

The present invention also provides a compound having the structure:

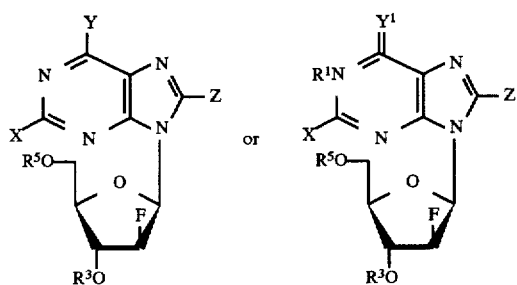

wherein
- $R^5$ is triphenylmethyl, diphenyl(4-methoxyphenyl)methyl, or phenyldi(4-methoxyphenyl)methyl;
- $R^3$ is hydrogen, trityl, triphenylmethyl, diphenyl(4-methoxyphenyl)methyl, phenyldi(4-methoxyphenyl)methyl, tetrahydropyranyl, acetyl, propanoyl, benzoyl, anisoyl, toluoyl, nitrobenzoyl, benzyl, toluyl, methoxybenzyl, or nitrobenzyl;
- $R^1$ is hydrogen, benzyl or a substituted benzyl group;
- X is hydrogen, a fluoro, an amino or a substituted amino;
- Y is hydrogen, a methoxy, a methylthio, a benzylthio, an isopropyl, a chloro, an amino or a substituted amino;
- Y' is an oxo or a thio group; and
- Z is hydrogen, a hydroxy, a methoxy, a halogen, an amino or a substituted amino;

Compounds having the above-identified structure, although not limited to the following compounds, may be selected from the group consisting of:

9-(3'-O-acetyl-2'-deoxy-2'-fluoro-5'-O-trityl-β-D-arabinofuranosyl) purine,
9-(3'-O-acetyl-2'-deoxy-2'-fluoro-5'-O-trityl-β-D-arabinofuranosyl)-6-chloropurine,
9-(3'-O-acetyl-2'-deoxy-2'-fluoro-5'-O-trityl-β-D-arabinofuranosyl)-6-thiopurine,
9-(3'-O-acetyl-2'-deoxy-2'-fluoro-5'-O-trityl-β-D-arabinofuranosyl)-6-methylthiopurine,
9-(3'-O-acetyl-2'-deoxy-2'-fluoro-5'-O-trityl-β-D-arabinofuranosyl)-6-aminomethylpurine,
9-(3'-O-acetyl-2'-deoxy-2'-fluoro-5'-O-trityl-β-D-arabinofuranosyl)-6-dimethylpurine,
9-(3'-O-acetyl-2'-deoxy-2'-fluoro-5'-O-trityl-β-D-arabinofuranosyl)-6-acetamidopurine,
9-(3'-O-acetyl-2'-deoxy-2'-fluoro-5'-O-trityl-β-D-arabinofuranosyl)-2-benzamidopurine,
9-(3'-O-acetyl-2'-deoxy-2'-fluoro-5'-O-trityl-β-D-arabinofuranosyl)-2-isobutanamidopurine,
9-(3'-O-acetyl-2'-deoxy-2'-fluoro-5'-O-trityl-β-D-arabinofuranosyl)-$N^2$-isobutyryl-6-thiopurine,
9-(3'-O-acetyl-2'-deoxy-2'-fluoro-5'-O-trityl-β-D-arabinofuranosyl)-2,6-diacetamidopurine,
9-(3'-O-acetyl-2'-deoxy-2'-fluoro-5'-O-trityl-β-D-arabinofuranosyl)-2,6-diabenzamidopurine,
9-(3'-O-acetyl-2'-deoxy-2'-fluoro-5'-O-trityl-β-D-arabinofuranosyl)-2,6-diisobutanamidopurine,
9-(3'-O-acetyl-2'-deoxy-2'-fluoro-5'-O-trityl-β-D-arabinofuranosyl)-2-acetamido-6-chloropurine,
9-(3'-O-acetyl-2'-deoxy-2'-fluoro-5'-O-trityl-β-D-arabinofuranosyl)-2-acetamido-6-thiopurine,
9-(3'-O-acetyl-2'-deoxy-2'-fluoro-5'-O-trityl-β-D-arabinofuranosyl)-2-acetamido-6-methylthiopurine,
9-(3'-O-acetyl-2'-deoxy-2'-fluoro-5'-O-trityl-β-D-arabinofuranosyl)-2-fluoropurine,
9-(3'-O-acetyl-2'-deoxy-2'-fluoro-5'-O-trityl-β-D-arabinofuranosyl)-2-fluoro-6-thiopurine,
9-(3'-O-acetyl-2'-deoxy-2'-fluoro-5'-O-trityl-β-D-arabinofuranosyl)-2-fluoro-6-methylthiopurine,
9-(3'-O-acetyl-2'-deoxy-2'-fluoro-5'-O-trityl-β-D-arabinofuranosyl)-2-fluoro-6-dimethylaminopurine,
9-(3'-O-acetyl-2'-deoxy-2'-fluoro-5'-O-trityl-β-D-arabinofuranosyl)adenine,
9-(3'-O-acetyl-2'-deoxy-2'-fluoro-5'-O-trityl-β-D-arabinofuranosyl)-N-acetyladenine,
9-(3'-O-acetyl-2'-deoxy-2'-fluoro-5'-O-trityl-β-D-arabinofuranosyl)-$N^6$-benzoyladenine,
9-(3'-O-acetyl-2'-deoxy-2'-fluoro-5'-O-trityl-β-D-arabinofuranosyl)-$N^6$-trityladenine,
9-(3'-O-acetyl-2'-deoxy-2'-fluoro-5'-O-trityl-β-D-arabinofuranosyl)-2-fluoroadenine,
9-(2'deoxy-2-fluoro-3',5'-di-O-trityl-β-D-arabinofuranosyl) purine,
9-(2'deoxy-2-fluoro-3',5'-di-O-trityl-β-D-arabinofuranosyl)-6-chloropurine,
9-(2'deoxy-2-fluoro-3',5'-di-O-trityl-β-D-arabinofuranosyl)-6-thiopurine,
9-(2'deoxy-2-fluoro-3',5'-di-O-trityl-β-D-arabinofuranosyl)-6-methylthiopurine,
9-(2'deoxy-2-fluoro-3',5'-di-O-trityl-β-D-arabinofuranosyl)-6-aminomethylpurine,
9-(2'deoxy-2-fluoro-3',5'-di-O-trityl-β-D-arabinofuranosyl)-6-dimethylaminopurine,
9-(2'deoxy-2-fluoro-3',5'-di-O-trityl-β-D-arabinofuranosyl)-2-aminopurine,
9-(2'deoxy-2-fluoro-3',5'-di-O-trityl-β-D-arabinofuranosyl)-2-benzamidopurine,
9-(2'deoxy-2-fluoro-3',5'-di-O-trityl-β-D-arabinofuranosyl)-2-isobytanamidopurine,
9-(2'deoxy-2-fluoro-3',5'-di-O-trityl-β-D-arabinofuranosyl)-2,6-diaminopurine,
9-(2'deoxy-2-fluoro-3',5'-di-O-trityl-β-D-arabinofuranosyl)-2,6-diacetamidopurine,
9-(2'deoxy-2-fluoro-3',5'-di-O-trityl-β-D-arabinofuranosyl)-2,6-dibenzamidopurine,
9-(2'deoxy-2-fluoro-3',5'-di-O-trityl-β-D-arabinofuranosyl)-2,6-diisobutanamidopurine,
9-(2'deoxy-2-fluoro-3',5'-di-O-trityl-β-D-arabinofuranosyl)-2-amino-6-chloropurine,
9-(2'deoxy-2-fluoro-3',5'-di-O-trityl-β-D-arabinofuranosyl)-2-amino-6-thiopurine,
9-(2'deoxy-2-fluoro-3',5'-di-O-trityl-β-D-arabinofuranosyl)-2-amino-6-methylthiopurine,
9-(2'deoxy-2-fluoro-3',5'-di-O-trityl-β-D-arabinofuranosyl)-2-fluoropurine,
9-(2'deoxy-2-fluoro-3',5'-di-O-trityl-β-D-arabinofuranosyl)-2-fluoro-6-thiopurine,
9-(2'deoxy-2-fluoro-3',5'-di-O-trityl-β-D-arabinofuranosyl)-2-fluoro-6-methylthiopurine,
9-(2'deoxy-2-fluoro-3',5'-di-O-trityl-β-D-arabinofuranosyl)-2-fluoro-6-aminomethylpurine,
9-(2'deoxy-2-fluoro-3',5'-di-O-trityl-β-D-arabinofuranosyl)-2-fluoro-6-dimethylaminopurine,
9-(2'deoxy-2-fluoro-3',5'-di-O-trityl-β-D-arabinofuranosyl)-2-fluoroadenine,
9-(2'deoxy-2-fluoro-3',5'-di-O-trityl-β-D-arabinofuranosyl)-$N^6$-trityladenine,
9-(2'deoxy-2-fluoro-3',5'-di-O-trityl-β-D-arabinofuranosyl)-N-acetyladenine,
9-(2'deoxy-2-fluoro-3',5'-di-O-trityl-β-D-arabinofuranosyl)-$N^6$-benzoyladenine,
9-(2'deoxy-2-fluoro-3',5'-di-O-trityl-β-D-arabinofuranosyl)-2-fluoroadenine,
9-(3'-O-acetyl-2'-deoxy-2'-fluoro-5'-O-trityl-β-D-arabinofuranosyl)-$N^2$-acetylguanine, 9-(3'-O-acetyl-2'-deoxy-2'-fluoro-5'-O-trityl-β-D-arabinofuranosyl)-$N^2$-benzoylguanine, 9-(3'-O-acetyl-2'-deoxy-2'-fluoro-5'-O-trityl-β-D-arabinofuranosyl)-$N^2$-isobutyrylguanine, 9-(3'-O-acetyl-2'-deoxy-2'-fluoro-5'-O-trityl-β-D-arabinofuranosyl)-$N^2$-acetyl-6-thioguanine, 9-(3'-O-acetyl-2'-deoxy-2'-fluoro-5'-O-trityl-β-D-arabinofuranosyl)-$N^2$-benzoyl-6-thioguanine, 9-(3'-O-acetyl-2'-deoxy-2'-fluoro-5'-O-trityl-β-D-arabinofuranosyl)-$N^2$-isobutyryl-6-thioguanine, 9-(3'-O-acetyl-2'-deoxy-2-fluoro-3',5'-di-O-trityl-β-D-arabinofuranosyl)-thioguanine, 9-(2'deoxy-2-fluoro-3',5'-di-O-trityl-β-D-arabinofuranosyl)-2-fluorohypoxanthine, 9-(2'deoxy-2-fluoro-3',5'-di-O-trityl-β-D-arabinofuranosyl)-hypoxanthine, 9-(2'deoxy-2-fluoro-3',5'-di-O-trityl-β-D-arabinofuranosyl)-guanine, 9-(2'deoxy-2-fluoro-3',5'-di-O-trityl-β-D-arabinofuranosyl)-$N^2$-acetylguanine, 9-(2'deoxy-2-fluoro-3',5'-di-O-trityl-β-D-arabinofuranosyl)-$N^2$-benzoylguanine, 9-(2'deoxy-2-fluoro-3',5'-di-O-trityl-β-D-arabinofuranosyl)-$N^2$-isobutrylguanine, or 9-(2'deoxy-2-fluoro-3',5'-di-O-trityl-β-D-arabinofuranosyl)-2-fluorohypoxanthine.

The following Experimental Detail Section and Examples are set forth to aid in an understanding of the invention. These sections are not intended to, and should not be construed to, limit in any way the invention set forth in the claims which follow thereafter.

Experimental Details

EXAMPLE 1

A mixture of 1-benzylinosine (3.58 g, 10 mmol) and trityl chloride (3.3 g, 12 mmol) in pyridine (50 mL is stirred overnight at room temperature. An additional amount of trityl chloride (3.3 g) is charged on the second and third days. The reaction is monitored by thin layer chromatography on silica gel plates using a mixture of chloroform and ethanol (10:1 v/v) as the developing solvent. After all the starting material is consumed, the mixture is concentrated in vacuo, and the residue coevaporated several times with toluene and ethanol, and then chromatographed on a silica column using chloroform-ethanol (19:1 v/v) as the eluent to give 5'-O-trityl-1-benzylinosine which is crystallized from ethanol: 5.40 g (90% yield), mp 208°–209° C. $^1$H NMR (Me$_2$SO-d$_6$) δ 3.20–3.24 (2H, m, H-5'.5"), 4.10–4.29 (2H, m, H-3',4'), 4.61–4.67 (1H, m, H-2', collapsed to dd upon addition of D$_2$O, $J_{1',2}$=5.6, $J_{2',3}$=5.0 Hz), 5.24 (2H, s, CH$_2$Ph), 5.21–5.27 (1H, m, OH, exchangeable), 5.57 (1H, d, OH), 5.92 (1H, d, H-1'), 7.06–7.32 (20H, m, Tr, CH$_2$Ph), 8.23, 8.51 (1H each, H-2, H-8). Analyses: calculated for C$_{26}$H$_{32}$N$_4$O$_5$: C, 71.98, H, 5.37, N, 9.33. Found: C, 71.86, H, 5.44, N, 9.18.

By following the same procedure but using the corresponding nucleosides, the following 5'-O-trityl nucleosides are prepared:

9-(5'-O-trityl-β-D-ribofuranosyl)purine,
9-(5'-O-trityl-β-D-ribofuranosyl)-6-chloropurine,
9-(5'-O-trityl-β-D-ribofuranosyl)-6-aminomethylpurine,
9-(5'-O-trityl-β-D-ribofuranosyl)-2-aminopurine,
9-(5'-O-trityl-β-D-ribofuranosyl)-2-acetamidopurine,
9-(5'-O-trityl-β-D-ribofuranosyl)-2-benzamidopurine,
9-(5'-O-trityl-β-D-ribofuranosyl)-2-isobutanamidopurine,
9-(5'-O-trityl-β-D-ribofuranosyl)-2,6-diaminopurine,
9-(5'-O-trityl-β-D-ribofuranosyl)-2,6-diacetamidopurine,
9-(5'-O-trityl-β-D-ribofuranosyl)-2,6-dibenzamidopurine,
9-(5'-O-trityl-β-D-ribofuranosyl)-2,6-diisobutanamidopurine,
9-(5'-O-trityl-β-D-ribofuranosyl)-2-amino-6-chloropurine,
9-(5'-O-trityl-β-D-ribofuranosyl)-2-amino-6-thiopurine,
9-(5'-O-trityl-β-D-ribofuranosyl)-2-amino-6-methylthiopurine,
9-(5'-O-trityl-β-D-ribofuranosyl)-2-fluropurine,
9-(5'-O-trityl-β-D-ribofuranosyl)-2-fluoroadenine,
9-(5'-O-trityl-β-D-ribofuranosyl)-2-fluorohypoxanthine,
9-(5'-O-trityl-β-D-ribofuranosyl)-2-fluoro-6-thiopurine,
9-(5'-O-trityl-β-D-ribofuranosyl)-2-fluoro-6-methylthiopurine,
9-(5'-O-trityl-β-D-ribofuranosyl)-2-fluoro-6-aminomethylpurine, and
9-(5'-O-trityl-β-D-ribofuranosyl)-2-fluoro-6-dimethylaminopurine.

EXAMPLE 2

A mixture of 5'-O-trityladenosine (497 mg, 1 mmol) and dibutyltin oxide (249 mg, 1 mmol) in methanol (50 mL) is heated under reflux until a clear solution is obtained. The solution is concentrated in vacuo, the residue dissolved in dimethylformamide (20 mL). To the ice cooled solution is added triflyl chloride (190 mg, 1.1 mmol), and the mixture stirred for 90 minutes at room temperature, and then concentrated in vacuo. The residue is dissolved in pyridine (20 mL), and the solution treated with acetic anhydride (1.5 mL). After being stirred for 3 hours at room temperature, the mixture is concentrated in vacuo. The residue is chromatographed on a silica gel using a mixture of chloroform and ethanol (33:1 v/v) as the eluent to give 3'-O-acetyl-2'-O-triflyl-5'-O-trityladenosine (208) mg, 31%) as a foam. $^1$H NMR (Me$_2$SO-d$_6$) δ 2.12 (3H, s, OAc), 3.36–3.49 (2H, m, H-5'5"), 4.36–4.40 (1H, m, H-4'), 5.90–5.95 (1h, m, H-3'), 6.45–6.54 (2H, m, H-1',2'), 7.20–7.57 (17H, m, Tr, NH$_2$), 8.06, 8.35 (1H each, s, H-2, H-8). Analyses: Calculated for C$_{32}$H$_{28}$F$_3$N$_5$O$_7$S: C, 71.94, H, 5.45, N, 10.24. Found: C, 71.67, H, 5.50, N, 10.27.

By following the same procedure but using the corresponding 5'-O-tritylnucleosides, the following 3'-O-acetyl-2'-O-triflyl-5'-O-tritylnucleosides are prepared:

9-(3'-O-acetyl-2'-O-triflyl-5'-O-trityl-β-D-ribofuranosyl)purine,
9-(3'-O-acetyl-2'-O-triflyl-5'-O-trityl-β-D-ribofuranosyl)-6-chloropurine,
9-(3'-O-acetyl-2'-O-triflyl-5'-O-trityl-β-D-ribofuranosyl)-6-thiopurine,
9-(3'-O-acetyl-2'-O-triflyl-5'-O-trityl-β-D-ribofuranosyl)-6-methylthiopurine,
9-(3'-O-acetyl-2'-O-triflyl-5'-O-trityl-β-D-ribofuranosyl)-6-aminomethylpurine,
9-(3'-O-acetyl-2'-O-triflyl-5'-O-trityl-β-D-ribofuranosyl)-6-dimethylaminopurine,
9-(3'-O-acetyl-2'-O-triflyl-5'-O-trityl-β-D-ribofuranosyl)-2-aminopurine,
9-(3'-O-acetyl-2'-O-triflyl-5'-O-trityl-β-D-ribofuranosyl)-2-acetamidopurine,
9-(3'-O-acetyl-2'-O-triflyl-5'-O-trityl-β-D-ribofuranosyl)-2-benzamidopurine,
9-(3'-O-acetyl-2'-O-triflyl-5'-O-trityl-β-D-ribofuranosyl)-2-isobutanamidopurine,
9-(3'-O-acetyl-2'-O-triflyl-5'-O-trityl-β-D-ribofuranosyl)-2,6-diaminopurine,
9-(3'-O-acetyl-2'-O-triflyl-5'-O-trityl-β-D-ribofuranosyl)-2,6-diacetamidopurine,
9-(3'-O-acetyl-2'-O-triflyl-5'-O-trityl-β-D-ribofuranosyl)-2,6-dibenzamidopurine, 9-(3'-O-acetyl-2'-O-triflyl-5'-O-trityl-β-D-ribofuranosyl)-2,6-diisobutanamidopurine, 9-(3'-O-acetyl-2'-O-triflyl-5'-O-trityl-β-D-ribofuranosyl)-2-amino-6-chloropurine, 9-(3'-O-acetyl-2'-O-triflyl-5'-O-trityl-β-D-ribofuranosyl)-2-amino-6-thiopurine, 9-(3'-O-acetyl-2'-O-triflyl-5'-O-trityl-β-D-ribofuranosyl)-2-amino-6-methylthiopurine, 9-(3'-O-acetyl-2'-O-triflyl-5'-O-trityl-β-D-ribofuranosyl)-2-fluoropurine, 9-(3'-O-acetyl-2'-O-triflyl-5'-O-trityl-β-D-ribofuranosyl)-2-fluoro-6-thiopurine, 9-(3'-O-acetyl-2'-O-triflyl-5'-O-trityl-β-D-ribofuranosyl)-2-fluoro-6-methylthiopurine, 9-(3'-O-acetyl-2'-O-triflyl-5'-O-trityl-β-D-ribofuranosyl)-2-fluoro-6-aminomethylpurine, 9-(3'-O-acetyl-2'-O-triflyl-5'-O-trityl-β-D-ribofuranosyl)-2-fluoro-6-dimethylaminopurine, 9-(3'-O-acetyl-2'-O-triflyl-5'-O-trityl-β-D-ribofuranosyl)-$N^6$-acetyladenine, 9-(3'-O-acetyl-2'-O-triflyl-5'-O-trityl-β-D-ribofuranosyl)-$N^6$-benzoyladenine, 9-(3'-O-acetyl-2'-O-triflyl-5'-O-trityl-β-D-ribofuranosyl)-$N^2$-trityladenine, 9-(3'-O-acetyl-2'-O-triflyl-5'-O-trityl-β-D-ribofuranosyl)-2-fluoroadenine, 9-(3'-O-acetyl-2'-O-triflyl-5'-O-trityl-β-D-ribofuranosyl)-1-benzylhypoxanthine, 9-(3'-O-acetyl-2'-O-triflyl-5'-O-trityl-β-D-ribofuranosyl)-2-acetamidoguanine, 9-(3'-O-acetyl-2'-O-triflyl-5'-O-trityl-β-D-ribofuranosyl)-2-benzamidoguanine, 9-(3'-O-acetyl-2'-O-triflyl-5'-O-trityl-β-D-ribofuranosyl)-2-isobutanamidoguanine, 9-(3'-O-acetyl-2'-O-triflyl-5'-O-trityl-β-D-ribofuranosyl)-2-acetamido-6-thioguanine, 9-(3'-O-acetyl-2'-O-triflyl-5'-O-trityl-β-D-ribofuranosyl)-2-benzamido-6-thioguanine, 9-(3'-O-acetyl-2'-O-triflyl-5'-O-trityl-β-D-ribofuranosyl)-2-isobutanamido-6-thioguanine, and 9-(3'-O-acetyl-2'-O-triflyl-5'-O-trityl-β-D-ribofuranosyl)-2-fluorohypoxanthine.

EXAMPLE 3

To a stirred solution of 3'-O-acetyl-2'-O-triflyl-5'-O-trityladenosine (1.0 g, 1.46 mmol) in dry methylene chloride (10 mL) is added a solution of TASF (1.2 g, 1.46 mmol) in methylene chloride (9 mL) in an argon atmosphere at −70° C. The mixture is allowed to warm to room temperature and the stirring is continued. After 24 hours of stirring, an additional amount of TASF (1.2 g) is charged, and the stirring is continued for another 24 hours. The reaction is quenched by addition of water (15 mL). The organic layer is separated, washed with water (5 mL), dried over sodium sulfate, and then concentrated in vacuo. The residue is placed on the top of a silica gel column, which is washed successively with chloroform containing 1% of ethanol, 3% of ethanol and then 5% ethanol. 4-Acetoxy-6-O-tritylfurfurol (220 mg, 37% yield, mp 79°–83° C. from n-hexane-ethylether) eluted first followed by 4-hydroxy-6-O-tritylfurfurol (80 mg, 15% yield, mp 119°–120° C. from n-hexane-ethylether), 9-(3'-O-acetyl-2'-deoxy-2'fluoro-5'-O-trityl-β-D-arabinofuranosyl)adenine (33 mg, 4% yield), a foam. $^1$H NMR (Me$_2$SO-d$_6$) δ 2.10 (3H, s, OAc), 3.38–3.40 (2H, m, H-5', 5"), 4.20–4.24 (1H, m, H-4'), 5.57 (1H, dm, H-3', $J_{3',F}$=16.1 Hz), 5.52 (1H, dm, H-2', $J_{2',F}$=51.6 Hz), 6.49 (1H, dd, $J_{1,2}$=3.8, $J_{1',F}$=17.0 Hz), 7.25–7.36 (15H, m, Tr), 8.07 (1H, d, H-8, $J_{8,F}$=2.5 Hz) 8.15 (1H, s, H-2). Analyses calculated for $C_{31}H_{28}F_3N_5O_4$: C, 67.26, H, 5.10, N, 12.65. Found: C, 67.30, H, 5.21, N, 12.50, and 9-(2',3'-di-O-acetyl-5'-O-trityl-β-D-arabinofuranosyl)-adenine (104 mg, 12% yield).

By following the same procedure but using the corresponding 3'-O-acetyl-2'-O-triflyl-5'-O-tritylnucleosides, the following 9-(3'-O-acetyl-2'-deoxy-2'-fluoro-5'-O-triyl-β-D-arabinofuranosyl)-nucleosides are prepared in 4 to 10% yield:

9-(3'-O-acetyl-2'-deoxy-2'-fluoro-5'-O-trityl-β-D-arabinofuranosyl)purine, 9-(3'-O-acetyl-2'-deoxy-2'-fluoro-5'-O-trityl-β-D-arabinofuranosyl)-6-chloropurine, 9-(3'-O-acetyl-2'-deoxy-2'-fluoro-5'-O-trityl-β-D-arabinofuranosyl)-6-thiopurine, 9-(3'-O-acetyl-2'-deoxy-2'-fluoro-5'-O-trityl-β-D-arabinofuranosyl)-6-methylthiopurine, 9-(3'-O-acetyl-2'-deoxy-2'-fluoro-5'-O-trityl-β-D-arabinofuranosyl)-6-aminomethylpurine, 9-(3'-O-acetyl-2'-deoxy-2'-fluoro-5'-O-trityl-β-D-arabinofuranosyl)-6-dimethylpurine, 9-(3'-O-acetyl-2'-deoxy-2'-fluoro-5'-O-trityl-β-D-arabinofuranosyl)-2-acetamidopurine, 9-(3'-O-acetyl-2'-deoxy-2'-fluoro-5'-O-trityl-β-D-arabinofuranosyl)-2-benzamidopurine, 9-(3'-O-acetyl-2'-deoxy-2'-fluoro-5'-O-trityl-β-D-arabinofuranosyl)-2-isobutanamidopurine, 9-(3'-O-acetyl-2'-deoxy-2'-fluoro-5'-O-trityl-β-D-arabinofuranosyl)-2,6-diacetamidopurine, 9-(3'-O-acetyl-2'-deoxy-2'-fluoro-5'-O-trityl-β-D-arabinofuranosyl)-2,6-dibenzamidopurine, 9-(3'-O-acetyl-2'-deoxy-2'-fluoro-5'-O-trityl-β-D-arabinofuranosyl)-2,6-diisobutanamidopurine, 9-(3'-O-acetyl-2'-deoxy-2'-fluoro-5'-O-trityl-β-D-arabinofuranosyl)-2-acetamido-6-chloropurine, 9-(3'-O-acetyl-2'-deoxy-2'-fluoro-5'-O-trityl-β-D-arabinofuranosyl)-2-acetamido-6-thiopurine, 9-(3'-O-acetyl-2'-deoxy-2'-fluoro-5'-O-trityl-β-D-arabinofuranosyl)-2-acetamido-6-methylthiopurine, 9-(3'-O-acetyl-2'-deoxy-2'-fluoro-5'-O-trityl-β-D-arabinofuranosyl)-2-fluoropurine, 9-(3'-O-acetyl-2'-deoxy-2'-fluoro-5'-O-trityl-β-D-arabinofuranosyl)-2-fluoro-6-thiopurine, 9-(3'-O-acetyl-2'-deoxy-2'-fluoro-5'-O-trityl-β-D-arabinofuranosyl)-2-fluoro-6-methylthiopurine, 9-(3'-O-acetyl-2'-deoxy-2'-fluoro-5'-O-trityl-β-D-arabinofuranosyl)-2-fluoro-6-aminomethylpurine, 9-(3'-O-acetyl-2'-deoxy-2'-fluoro-5'-O-trityl-β-D-arabinofuranosyl)-2-fluoro-6-dimethylaminopurine, 9-(3'-O-acetyl-2'-deoxy-2'-fluoro-5'-O-trityl-β-D-arabinofuranosyl)-$N^6$-acetyladenine, 9-(3'-O-acetyl-2'-deoxy-2'-fluoro-5'-O-trityl-β-D-arabinofuranosyl)-$N^6$-benzoyladenine, 9-(3'-O-acetyl-2'-deoxy-2'-fluoro-5'-O-trityl-β-D-arabinofuranosyl)-N-trityladenine, 9-(3'-O-acetyl-2'-deoxy-2'-fluoro-5'-O-trityl-β-D-arabinofuranosyl)-2-fluoroadenine, 9-(3'-O-acetyl-2'-deoxy-2'-fluoro-5'-O-trityl-β-D-arabinofuranosyl)-$N^2$-acetylguanine, 9-(3'-O-acetyl-2'-deoxy-2'-fluoro-5'-O-trityl-β-D-arabinofuranosyl)-$N^2$-benzoylguanine, 9-(3'-O-acetyl-2'-deoxy-2'-fluoro-5'-O-trityl-β-D-arabinofuranosyl)-$N^2$-isobutyrylguanine, 9-(3'-O-acetyl-2'-deoxy-2'-fluoro-5'-O-trityl-β-D-arabinofuranosyl)-$N^2$-acetyl-6-thioguanine, 9-(3'-O-acetyl-2'-deoxy-2'-fluoro-5'-O-trityl-β-D-arabinofuranosyl)-$N^2$-benzoyl-6-thioguanine, and 9-(3'-O-acetyl-2'-deoxy-2¹-fluoro-5'-O-trityl-β-D-arabinofuranosyl)-N²-isobutyryl-6-thioguanine.

EXAMPLE 4

A mixture of 1-benzlinosine (50.0 g, 0.14 mol), 4-dimethylaminopyridine (25.3 g, 0.21 mol) and trityl chloride (97.2 g, 0.35 mol) in pyridine (550 mL) is heated at 70°–80° C. for 3 days. An additional amount of trityl chloride (58.3 g) and dimethylamino-pyridine (10 g) is charged after 24 hours of reaction, and another charge of trityl chloride (39 g) and dimethylaminopyridine (6.0 g) after 48 hours. The reaction mixture is filtered while hot, the filtrate is concentrated in vacuo, and the residue coevaporated with toluene (2×300 mL). The residue is chromatographed on a silica gel column (40×10 cm) using n-hexane-ethyl acetate (1:1 v/v) as the eluent followed by n-hexane-ethyl acetate (1:1 v/v) containing increasing amount of ethanol from 3% to 30%.

Fractions containing di-O-tritylnucleosides are combined, concentrated in vacuo, and the residue rechromatographed on a silica gel column using n-hexane-chloroform-ethanol (20:20:1 v/v/v) followed by n-hexane-chloroform-ethanol (10:20:1 v/v/v) as the eluents.

2',5'-di-O-trityl-1-benzlinosine, which is eluted first from the column, is obtained as colorless crystals after recrystallization from n-hexane-ethyl acetate (28.0 g, 24% yield); mp 231°–233° C., ¹H NMR (Me₂SO-d₆) δ 3.00–3.06 (2H, m, H-5', 5"), 3.20–3.24 (1H, m, H-4'), 4.05–4.09 (1H, m, H-3'), 4.95–5.02 (1H, m, H-2'), 5.15–5.22 (1H, m, OH), 5.22 (2H, m, CH₂Ph), 5.96 (1H, d, H-1', J₁',₂'=6.2 Hz), 7.02–7.64 (35H, 2×Tr and CH₂Ph), 8.08, 8.17 (1H each, s, H-2, H-8).

Analyses calculated for C₅₅H₄₆N₄O₅: C, 78.36, H, 5.50, N, 6.65. Found: C, 78.17, H, 5.36, N, 6.40.

3',5'-di-O-trityl-1-benzylinosine, which is eluted from the column next, is also obtained as colorless crystals (22.0 g, 19% yield), mp 187°–188° C., ¹H NMR (Me₂SO-d₆) δ 2.64–2.68 (2H, m, H-5'5"), 3.09–3.11 (1H, m, H-4'), 4.12–4.14 (1H, m, H-3'), 4.70–4.77 (1H, m, H-2'), 5.25 (2H, s, CH₂Ph), 6.10 (1H, d, H-1', J₁',₂'=7.2 Hz), 7.19–7.40 (35H, m, 2×Tr and CH₂Ph), 8.15, 8.42 (1H each, s, H-2, H-8). Analyses calculated for C₅₅H₄₆N₄O₅: C, 78.36, H, 5.50, N, 6.65. Found: C, 78.20, H, 5.41, N, 6.52.

By following the same procedure but using the corresponding nucleosides, the following 2',5'-di-O-trityl and 3',5'-di-O-trityl nucleosides may be prepared in 15 to 33% yield:

9-(2',5'-di-O-trityl-β-D-ribofuranosyl)-hypoxanthine,
9-(2',5'-di-O-trityl-β-D-ribofuranosyl) -N⁶-trityladenine,
9-(2',5'-di-O-trityl-β-D-ribofuranosyl)-N⁶-acetyladenine,
9-(2',5'-di-O-trityl-β-D-ribofuranosyl) -N⁶-benzoyladenine,
9-(2',5'-di-O-trityl-β-D-ribofuranosyl) -N²-tritylguanine,
9-(2',5'-di-O-trityl-β-D-ribofuranosyl) -N²-acetylguanine,
9-(2',5'-di-O-trityl-β-D-ribofuranosyl) -N²-benzoylguanine,
9-(2',5'-di-O-trityl-β-D-ribofuranosyl)-N²-isobutyrylguanine,
9-(2',5'-di-O-trityl-β-D-ribofuranosyl)purine,
9-(2',5'-di-O-trityl-β-D-ribofuranosyl)-6-chloropurine,
9-(2',5'-di-O-trityl-β-D-ribofuranosyl)-6-thiopurine,
9-(2',5'-di-O-trityl-β-D-ribofuranosyl)-6-methylthiopurine,
9-(2',5'-di-O-trityl-β-D-ribofuranosyl)-6-aminomethylpurine,
9-(2',5'-di-O-trityl-β-D-ribofuranosyl)-6-dimethylaminopurine,
9-(2',5'-di-O-trityl-β-D-ribofuranosyl)-2-aminopurine,
9-(2',5'-di-O-trityl-β-D-ribofuranosyl)-2-acetamidopurine,
9-(2',5'-di-O-trityl-β-D-ribofuranosyl)-2-benzamidopurine,
9-(2',5'-di-O-trityl-β-D-ribofuranosyl)-2-isobutanamidopurine,
9-(2',5'-di-O-trityl-β-D-ribofuranosyl)-2,6-diaminopurine,
9-(2',5'-di-O-trityl-β-D-ribofuranosyl)-2,6-diacetamidopurine,
9-(2',5'-di-O-trityl-β-D-ribofuranosyl)-2,6-dibenzamidopurine,
9-(2',5'-di-O-trityl-β-D-ribofuranosyl)-2,6-diisobutanamidopurine,
9-(2',5'-di-O-trityl-β-D-ribofuranosyl)-2-amino-6-chloropurine,
9-(2',5'-di-O-trityl-β-D-ribofuranosyl)-2-amino-6-thiopurine,
9-(2',5'-di-O-trityl-β-D-ribofuranosyl)-2-amino-6-methylthiopurine,
9-(2',5'-di-O-trityl-β-D-ribofuranosyl)-2-fluoropurine,
9-(2',5'-di-O-trityl-β-D-ribofuranosyl)-2-fluoroadenine,
9-(2',5'-di-O-trityl-β-D-ribofuranosyl)-2-fluorohypoxanthine,
9-(2',5'-di-O-trityl-β-D-ribofuranosyl)-2-fluoro-6-thiopurine,
9-(2',5'-di-O-trityl-β-D-ribofuranosyl)-2-fluoro-6-methylthiopurine,
9-(2',5'-di-O-trityl-β-D-ribofuranosyl)-2-fluoro-6-aminomethylpurine,
9-(2',5'-di-O-trityl-β-D-ribofuranosyl)-2-fluoro-6-dimethylaminopurine.
9-(3',5'-di-O-trityl-β-D-ribofuranosyl)-hypoxanthine,
9-(3',5'-di-O-trityl-β-D-ribofuranosyl)-N⁶-trityladenine,
9-(3',5'-di-O-trityl-β-D-ribofuranosyl)-N⁶-acetyladenine,
9-(3',5'-di-O-trityl-β-D-ribofuranosyl)-N⁶-benzoyladenine,
9-(3',5'-di-O-trityl-β-D-ribofuranosyl)-N²-tritylguanine,
9-(3',5'-di-O-trityl-β-D-ribofuranosyl)-N²-acetylguanine,
9-(3',5'-di-O-trityl-β-D-ribofuranosyl)-N²-benzoylguanine,
9-(3',5'-di-O-trityl-β-D-ribofuranosyl)-N²-isobutyrlguanine,
9-(3',5'-di-O-trityl-β-D-ribofuranosyl)purine,
9-(3',5'-di-O-trityl-β-D-ribofuranosyl)-6-chloropurine,
9-(3',5'-di-O-trityl-β-D-ribofuranosyl)-6-thiopurine,
9-(3',5'-di-O-trityl-β-D-ribofuranosyl)-6-methylthiopurine,
9-(3',5'-di-O-trityl-β-D-ribofuranosyl)-6-aminomethylpurine,
9-(3',5'-di-O-trityl-β-D-ribofuranosyl)-6-dimethylaminopurine,
9-(3',5'-di-O-trityl-β-D-ribofuranosyl)-2-aminopurine,
9-(3',5'-di-O-trityl-β-D-ribofuranosyl)-2-acetamidopurine,
9-(3',5'-di-O-trityl-β-D-ribofuranosyl)-2-benzamidopurine,
9-(3',5'-di-O-trityl-β-D-ribofuranosyl)-2-isobutanamidopurine,
9-(3',5'-di-O-trityl-β-D-ribofuranosyl)-2,6-diaminopurine,
9-(3',5'-di-O-trityl-β-D-ribofuranosyl)-2,6-diacetamidopurine,
9-(3',5'-di-O-trityl-β-D-ribofuranosyl)-2,6-dibenzamidopurine,
9-(3',5'-di-O-trityl-β-D-ribofuranosyl)-2,6-diisobutanamidopurine,
9-(3',5'-di-O-trityl-β-D-ribofuranosyl)-2-amino-6-chloropurine,
9-(3',5'-di-O-trityl-β-D-ribofuranosyl)-2-amino-6-thiopurine,
9-(3',5'-di-O-trityl-β-D-ribofuranosyl)-2-amino-6-methylthiopurine,
9-(3',5'-di-O-trityl-β-D-ribofuranosyl)-2-fluoropurine,
9-(3',5'-di-O-trityl-β-D-ribofuranosyl)-2-fluoroadenine,
9-(3',5'-di-O-trityl-β-D-ribofuranosyl)-2-fluorohypoxanthine,
9-(3',5'-di-O-trityl-β-D-ribofuranosyl)-2-fluoro-6-thiopurine, 9-(3',5'-di-O-trityl-β-D-ribofuranosyl)-2-fluoro-6-methylthiopurine, 9-(3',5'-di-O-trityl-β-D-ribofuranosyl)-2-fluoro-6-aminomethylpurine, and 9-(3',5'-di-O-trityl-β-D-ribofuranosyl)-2-fluoro-6-dimethylaminopurine.

EXAMPLE 5

To a solution of 3',5'-di-O-trityl-1-benzylinosine (2.0 g, 2.4 mmol), 4-dimethylaminopyridine (290 mg, 2.4 mmol) and triethylamine (480 mg, 4.8 mmol) in methylene chloride (40 mL) is added triflyl chloride (800 mg, 4.8 mmol), and the mixture is stirred at room temperature for 1 hour, and then concentrated in vacuo. The residue is chromatographed on a silica gel column using a mixture of tetrachloromethane and ethyl acetate (5:1 v/v) as the eluent to give 3',5'-di-O-trityl-2'-O-triflyl-1-benzylinosine as a foam (1.82 g, 78% yield). $^1$H NMR (Me$_2$SO-d$_6$) δ 2.92–2.96 (2H, m, H-5',5"), 3.62–3.69 (1H, m, H-4'), 4.41–4.43 (1H, m, H-3'), 5.23 (2H, s, CH$_2$Ph), 5.89–5.95 (1H, m, H-2'), 6.66 (1H, d, H-1', J$_{1',2}$=6.3 Hz), 7.18–7.34 (35H, m, 2×Tr and CH$_2$Ph), 8.29, 8.32 (1H each, s, H-2, H-8). Analyses calculated for C$_{56}$H$_{45}$F$_3$N$_4$O$_5$S: C, 68.98, H, 4.65, N, 5.63. Found: C, 68.94, H, 4.76, N, 5.63.

By following the same procedure but using the corresponding 3',5'-di-O-trityl nucleosides, the following 2'-O-triflyl-3',5'-di-O-trityl nucleosides are prepared:

9-(2'-O-triflyl-3',5'-di-O-trityl-β-D-ribofuranosyl) hypoxanthine, 9-(2'-O-triflyl-3',5'-di-O-trityl-β-D-ribofuranosyl)-2-fluorohypoxanthine, 9-(2'-O-triflyl-3',5'-di-O-trityl-β-D-ribofuranosyl)-6-thiohypoxanthine, 9-(2'-O-triflyl-3',5'-di-O-trityl-β-D-ribofuranosyl)-N$^6$-trityladenine, 9-(2'-O-triflyl-3',5-di-O-trityl-β-D-ribofuranosyl)-N$^6$-acetyladenine, 9-(2'-O-triflyl-3',5'-di-O-trityl-β-D-ribofuranosyl)-N$^6$-benzoladenine, 9-(2'-O-triflyl-3',5'-di-O-trityl-β-D-ribofuranosyl)-N$^2$-tritylguanine, 9-(2'-O-triflyl-3',5'-di-O-trityl-β-D-ribofuranosyl)-N$^2$-acetylguanine, 9-(2'-O-triflyl-3',5'-di-O-trityl-β-D-ribofuranosyl)-N$^2$-isobutyrylguanine, 9-(2'-O-triflyl-3',5'-di-O-trityl-β-D-ribofuranosyl)-N$^2$-benzoylguanine, 9-(2'-O-triflyl-3',5'-di-O-trityl-β-D-ribofuranosyl)-N$^2$-trityl-6-thioguanine, 9-(2'-O-triflyl-3',5'-di-O-trityl-β-D-ribofuranosyl)-6-thio-N$^2$-acetylguanine, 9-(2'-O-triflyl-3',5'-di-O-trityl-β-D-ribofuranosyl)-6-thio-N$^2$-benzoylguanine, 9-(2'-O-triflyl-3',5'-di-O-trityl-β-D-ribofuranosyl)-6-thio-N$^2$-isobutyrylguanine, 9-(2'-O-triflyl-3',5'-di-O-trityl-β-D-ribofuranosyl)purine, 9-(2'-O-triflyl-3',5'-di-O-trityl-β-D-ribofuranosyl)-6-chloropurine, 9-(2'-O-triflyl-3',5'-di-O-trityl-β-D-ribofuranosyl)-6-thiopurine, 9-(2'-O-triflyl-3',5'-di-O-trityl-β-D-ribofuranosyl)-6-methylthiopurine, 9-(2'-O-triflyl-3',5'-di-O-trityl-β-D-ribofuranosyl)-6-aminomethylpurine, 9-(2'-O-triflyl-3',5'-di-O-trityl-β-D-ribofuranosyl)-6-dimethylaminopurine, 9-(2'-O-triflyl-3',5'-di-O-trityl-β-D-ribofuranosyl)-2-aminopurine, 9-(2'-O-triflyl-3',5'-di-O-trityl-β-D-ribofuranosyl)-2-acetamidopurine, 9-(2'-O-triflyl-3',5'-di-O-trityl-β-D-ribofuranosyl)-2-benzamidopurine, 9-(2'-O-triflyl-3',5'-di-O-trityl-β-D-ribofuranosyl)-2-isobutanamidopurine, 9-(2'-O-triflyl-3',5'-di-O-trityl-β-D-ribofuranosyl)-2,6-diaminopurine, 9-(2'-O-triflyl-3',5'-di-O-trityl-β-D-ribofuranosyl)-2,6-diacetamidopurine, 9-(2'-O-triflyl-3',5'-di-O-trityl-β-D-ribofuranosyl)-2,6-dibenzamidopurine, 9-(2'-O-triflyl-3',5'-di-O-trityl-β-D-ribofuranosyl)-2,6-diisobutanamidopurine, 9-(2'-O-triflyl-3',5'-di-O-trityl-β-D-ribofuranosyl)-2-amino-6-chloropurine, 9-(2'-O-triflyl-3',5'-di-O-trityl-β-D-ribofuranosyl)-2-amino-6-thiopurine, 9-(2'-O-triflyl-3',5'-di-O-trityl-β-D-ribofuranosyl)-2-amino-6-methylthiopurine, 9-(2'-O-triflyl-3',5'-di-O-trityl-β-D-ribofuranosyl)-2-fluoropurine, 9-(2'-O-triflyl-3',5'-di-O-trityl-β-D-ribofuranosyl)-2-fluoroadenine, 9-(2'-O-triflyl-3',5'-di-O-trityl-β-D-ribofuranosyl)-2-fluorohypoxanthine, 9-(2$^1$-O-triflyl-3',5'-di-O-trityl-β-D-ribofuranosyl)-2-fluoro-6-thiopurine, 9-(2'-O-triflyl-3',5'-di-O-trityl-β-D-ribofuranosyl)-2-fluoro-6-methylthiopurine, 9-(2'-O-triflyl-3',5'-di-O-trityl-β-D-ribofuranosyl)-2-fluoro-6-aminomethylpurine, 9-(2'-O-triflyl-3',5'-di-O-trityl-β-D-ribofuranosyl)-2-fluoro-6-dimethylaminopurine, 9-(3'-O-triflyl-2',5'-di-O-trityl-β-D-ribofuranosyl)purine, 9-(3'-O-triflyl-2',5'-di-O-trityl-β-D-ribofuranosyl) hypoxanthine, 9-(3'-O-triflyl-2',5'-di-O-trityl-β-D-ribofuranosyl)-2-fluorohypoxanthine, 9-(3'-O-triflyl-2',5'-di-O-trityl-β-D-ribofuranosyl)-6-thiohypoxanthine, 9-(3'-O-triflyl-2',5'-di-O-trityl-β-D-ribofuranosyl)-N$^6$-trityladenine, 9-(3'-O-triflyl-2',5'-di-O-trityl-β-D-ribofuranosyl)-N$^6$-acetyladenine, 9-(3'-O-triflyl-2',5'-di-O-trityl-β-D-ribofuranosyl)-N$^6$-benzoyladenine, 9-(3'-O-triflyl-2',5'-di-O-trityl-β-D-ribofuranosyl)-N$^2$-tritylguanine, 9-(3'-O-triflyl-2',5'-di-O-trityl-β-D-ribofuranosyl)-N$^2$-acetylguanine, 9-(3'-O-triflyl-2',5'-di-O-trityl-β-D-ribofuranosyl)-N$^2$-benzoylguanine, 9-(3'-O-triflyl-2',5'-di-O-trityl-β-D-ribofuranosyl)-N$^2$-isobutyrylguanine, 9-(3'-O-triflyl-2',5'-di-O-trityl-β-D-ribofuranosyl)-N$^2$-trityl-6-thioguanine, 9-(3'-O-triflyl-2',5'-di-O-trityl-β-D-ribofuranosyl)-6-thio-N$^2$-acetylguanine, 9-(3'-O-triflyl-2',5'-di-O-trityl-β-D-ribofuranosyl)-6-thio-N$^2$-benzoylguanine, 9-(3'-O-triflyl-2',5'-di-O-trityl-β-D-ribofuranosyl)-6-thio-N$^2$-isobutyrylguanine, 9-(3'-O-triflyl-2',5'-di-O-trityl-β-D-ribofuranosyl)-6-chloropurine, 9-(3'-O-triflyl-2',5'-di-O-trityl-β-D-ribofuranosyl)-6-thiopurine, 9-(3'-O-triflyl-2',5'-di-O-trityl-β-D-ribofuranosyl)-6-methylthiopurine, 9-(3'-O-triflyl-2',5'-di-O-trityl-β-D-ribofuranosyl)-6-aminomethylpurine, 9-(3'-O-triflyl-2',5'-di-O-trityl-β-D-ribofuranosyl)-6-dimethylaminopurine, 9-(3'-O-triflyl-2',5'-di-O-trityl-β-D-ribofuranosyl)-2-aminopurine, 9-(3'-O-triflyl-2',5'-di-O-trityl-β-D-ribofuranosyl)-2,6-diaminopurine, 9-(3'-O-triflyl-2',5'-di-O-trityl-β-D-ribofuranosyl)-2-amino-6-chloropurine, 9-(3'-O-triflyl-2',5'-di-O-trityl-β-D-ribofuranosyl)-2-amino-6-thiopurine, 9-(3'-O-triflyl-2',5'-di-O-trityl-β-D-ribofuranosyl)-2-amino-6-methylthiopurine, 9-(3'-O-triflyl-2',5'-di-O-trityl-β-D-ribofuranosyl)-2-fluoropurine, 9-(3'-O-triflyl-2',5'-di-O-trityl-β-D-ribofuranosyl)-2-fluoroadenine, 9-(3'-O-triflyl-2',5'-di-O-trityl-β-D-ribofuranosyl)-2-fluorohypoxanthine, 9-(3'-O-triflyl-2',5'-di-O-trityl-β-D-ribofuranosyl)-2-fluoro-6-thiopurine, 9-(3'-O-triflyl-2',5'-di-O-trityl-β-D-ribofuranosyl)-2-fluoro-6-methylthiopurine, 9-(3'-O-triflyl-2',5'-di-O-trityl-β-D-ribofuranosyl)-2-fluoro-6-aminomethylpurine, and 9-(3'-O-triflyl-2',5'-di-O-trityl-β-D-ribofuranosyl)-2-fluoro-6-dimethylaminopurine.

EXAMPLE 6

To a solution of 2'-O-triflyl-3',5'-di-O-trityl-1-benzylinosine (3.24 g, 3.32 mmol) in dry methylene chloride (40 mL) is added a solution of TASF (2.75 g, 10 mmol) in methylene chloride (20 mL) in an argon atmosphere at −70° C. The reaction mixture is allowed to warm to room temperature, and stirring contained for 4 days. An additional amount of TASF (5.0 g, 20 mmol) in methylene chloride (40 mL) is charged at −40° C. on the second and third days. The reaction is quenched by addition of water (50 mL). The organic layer is separated, washed with water (2×75 mL), dried over sodium sulfate, and concentrated in vacuo. The residue is chromotographed on a silica gel column using n-hexane-ethyl acetate (4:1 v/v) as the initial eluent followed by n-hexane-ethyl acetate (2:1 v/v) to give 9-(2'deoxy-2'-fluoro-3',5'-di-O-trityl-β-D-arabinofuranosyl)-1-benzylhypoxanthine (842 mg, 30% yield) as a foam. $^1$H NMR (Me$_2$SO-d$_6$) δ 3.00–3.02 (2H, m, H-5',5"), (1H, dm, H-3', J$_{3',F}$=19.5 Hz), 4.39 (1H, m, H-4'), 4.44 (1H, dm, H-2', J$_{2',F}$=50 0 Hz), 5.24 (2H, s, CH$_2$Ph), 6.37 (1H, dd, H-1', J$_{1',2}$=3.0, J$_{1'}$, F=22.0 Hz), 7.27–7.32 (35H, m, 2×Tr and Ch$_2$Ph), 7.72 (1H, d, H-8, J$_{8,F}$=2.2 Hz), 8.56 (1H, s, H-2). Analyses calculated for C$_{55}$H$_{45}$FN$_4$O$_4$.1/5CHCl$_3$: C, 76.31, H, 5.24, N, 6.45. Found: C, 76.45, H, 5.54, N, 6.23. A small amount of chloroform is detected in the $^1$H NMR of this analytical sample.

By following the same procedure but using the corresponding 2'-O-triflyl-3',5'-di-O-trityl nucleosides, the following 9-(2'-deoxy-2'-3',5'-di-O-trityl nucleosides are prepared in 6–30% yield:

9-(2'deoxy-2'-fluoro-3',5'-di-O-trityl-β-D-arabinofuranosyl)-purine, 9-(2'deoxy-2'-fluoro-3',5'-di-O-trityl-β-D-arabinofuranosyl)-thioguanine, 9-(2'deoxy-2'-fluoro-3',5'-di-O-trityl-β-D-arabinofuranosyl)-2-fluoroadenine, 9-(2'deoxy-2'-fluoro-3',5'-di-O-trityl-β-D-arabinofuranosyl)-2-fluorohypoxanthine, 9-(2'deoxy-2'-fluoro-3',5'-di-O-trityl-β-D-arabinofuranosyl)-N$^6$-trityladenine, 9-(2'deoxy-2'-fluoro-3',5'-di-O-trityl-β-D-arabinofuranosyl)-N$^6$-acetyladenine, 9-(2'deoxy-2'-fluoro-3',5'-di-O-trityl-β-D-arabinofuranosyl)-N$^6$-benzoyladenine, 9-(2'deoxy-2'-fluoro-3',5'-di-O-trityl-β-D-arabinofuranosyl)-hypoxanthine, 9-(2'deoxy-2'-fluoro-3',5'-di-O-trityl-β-D-arabinofuranosyl)-guanine, 9-(2'deoxy-2'-fluoro-3',5'-di-O-trityl-β-D-arabinofuranosyl)-N$^2$-acetylguanine, 9-(2'deoxy-2'-fluoro-3',5'-di-O-trityl-β-D-arabinofuranosyl)-N$^2$-benzoylguanine, 9-(2'deoxy-2'-fluoro-3',5'-di-O-trityl-β-D-arabinofuranosyl)-N$^2$-isobutyrylguanine, 9-(2'deoxy-2'-fluoro-3',5'-di-O-trityl-β-D-arabinofuranosyl)-6-chloropurine, 9-(2'deoxy-2'-fluoro-3',5'-di-O-trityl-β-D-arabinofuranosyl)-6-thiopurine, 9-(2'deoxy-2'-fluoro-3',5'-di-O-trityl-β-D-arabinofuranosyl)-6-methylthiopurine, 9-(2'deoxy-2'-fluoro-3',5'-di-O-trityl-β-D-arabinofuranosyl)-6-aminomethylpurine, 9-(2'deoxy-2'-fluoro-3',5'-di-O-trityl-β-D-arabinofuranosyl)-6-dimethylaminopurine, 9-(2'deoxy-2'-fluoro-3',5'-di-O-trityl-β-D-arabinofuranosyl)-2-aminopurine, 9-(2'deoxy-2'-fluoro-3',5'-di-O-trityl-β-D-arabinofuranosyl)-2-acetamidopurine, 9-(2'deoxy-2'-fluoro-3',5'-di-O-trityl-β-D-arabinofuranosyl)-2-benzamidopurine, 9-(2'deoxy-2'-fluoro-3',5'-di-O-trityl-β-D-arabinofuranosyl)-2-isobytanamidopurine, 9-(2'deoxy-2'-fluoro-3',5'-di-O-trityl-β-D-arabinofuranosyl)-2,6-diaminopurine, 9-(2'deoxy-2'-fluoro-3',5'-di-O-trityl-β-D-arabinofuranosyl)-2,6-diacetamidopurine, 9-(2'deoxy-2'-fluoro-3',5'-di-O-trityl-β-D-arabinofuranosyl)-2,6-diabenzamidopurine, 9-(2'deoxy-2'-fluoro-3',5'-di-O-trityl-β-D-arabinofuranosyl)-2,6-diisobutanamidopurine, 9-(2'deoxy-2'-fluoro-3',5'-di-O-trityl-β-D-arabinofuranosyl)-2-amino-6-chloropurine, 9-(2'deoxy-2$^1$-fluoro-3',5'-di-O-trityl-β-D-arabinofuranosyl)-2-amino-6-thiopurine, 9-(2'deoxy-2'-fluoro-3',5'-di-O-trityl-β-D-arabinofuranosyl)-2-amino-6-methylthiopurine, 9-(2'deoxy-2'-fluoro-3',5'-di-O-trityl-β-D-arabinofuranosyl)-2-fluoropurine, 9-(2'deoxy-2'-fluoro-3',5'-di-O-trityl-β-D-arabinofuranosyl)-2-fluoroadenine, 9-(2'deoxy-2'-fluoro-3',5'-di-O-trityl-β-D-arabinofuranosyl)-2-fluorohypoxanthine, 9-(2'deoxy-2'-fluoro-3',5'-di-O-trityl-β-D-arabinofuranosyl)-2-fluoro-6-thiopurine, 9-(2'deoxy-2'-fluoro-3',5'-di-O-trityl-β-D-arabinofuranosyl)-2-fluoro-6-methylthiopurine, 9-(2'deoxy-2'-fluoro-3',5'-di-O-trityl-β-D-arabinofuranosyl)-2-fluoro-6-aminomethylpurine, and 9-(2'deoxy-2'-fluoro-3',5'-di-O-trityl-β-D-arabinofuranosyl)-2-fluoro-6-dimethylaminopurine.

Treatment of 2'-O-triflyl nucleosides with fluorinating agents other than TASF, such as potassium fluoride in dimethylformamide, or tetra-n-butlammonium fluoride in tetrahydrofuran. Amberlyst A26 (F) in methylene chloride, or cesium fluoride in dimethylformamide afforded the corresponding 2'-fluoro-arabino nucleosides but in much smaller yields.

EXAMPLE 7

To a solution of 3',5'-di-O-trityl-1-benzylinosine (4.3 g, 5.1 mmol) in dry methylene chloride (65 mL) is added a solution of DAST (2.02 mL, 15.3 mmol) in methylene chloride (65 mL) containing pyridine (3.7 mL, 50 mL) below −50° C. while stirring. The mixture is allowed to warm to room temperature, and the stirring continued for 18 hours. The mixture is concentrated in vacuo, and the residue chromoatographed on a silica gel column using a mixture of petroleum ether and ethyl acetate (1:1 v/v) as the eluent to give 9-(2'-deoxy-2'-fluoro-3',5'-di-O-trityl-β-D-arabinofuranosyl)-1-benzylhypoxanthine (2.27 g, 52.6% yield) which has identified $^1$H NMR characteristics with that of an authentic sample obtained as described in Example 6.

By following the same procedure but using the corresponding 3',5'-di-O-trityl nucleosides, the 9-(2'-deoxy-2'-fluoro-3',5'-di-O-trityl-β-D-arabinofuranosyl) nucleosides listed in Example 6 are prepared in 30–60% yield:

EXAMPLE 8

To a stirring mixture of trifluoroacetic acid (61.3 mL) and chloroform (670 mL) is added 9-(2'-deoxy-2'-fluoro-3',5'-di-O-trityl-β-D-arabinofuranosyl)-1-benzylhypoxanthine (6.63 g, 7.85 mmol) at −25° C. in an argon atmosphere. The mixture is allowed to warm to room temperature while stirring. After one hour at room temperature, the reaction mixture is cooled to −25° C., and then diluted with ethanol (70 mL). The mixture is concentrated in vacuo, the residue triturated with a mixture of n-hexane and ethyl ether (1:1 v/v) (2×400 mL). The solid residue is dissolved in a minimum amount of ethanol chromatographed over a silica gel column using a mixture of chloroform and ethanol (1:1 v/v) as the eluent to give 9-(2'-deoxy-2'-fluoro-β-D-arabinofuranosyl)-1-benzylhypoxanthine as a foam (2.5 g, 88% yield). $^1$H NMR (Me$_2$SO-d$_6$) δ 3.68–3.92 (3h, m, H-4',5',5"), 4.44 (1H, ddd, H-3', J$_{2',3}$=4.4, J$_{3',4}$=4.9, J$_{3',F}$=18.9 Hz), 5.23 (1h, ddd, H-2', J$_{2',3}$=4.7, J$_{2',3}$=4.4, J$_{2',F}$=53.7 Hz), 5.24 (2H, s, CH$_2$Ph), 6.39 (dd, H-1', J$_{1',2}$=4.7, J$_{1',F}$=13.5 Hz), 7.33 (5h, s, CH$_2$Ph), 8.26 (1H, d, H-8, J$_{8,F}$=1.9 Hz), 8.62 (1H, s, H-2). Analyses calculated for C$_{17}$H$_{17}$FN$_4$O$_4$: C, 56.66, H, 4.75, N, 15.55. Found: C, 56.21, H, 4.91, N, 15.12.

By following the same procedure but using the corresponding nucleosides, the following 2'deoxy-2'-fluoro-β-D-arabinofuranosyl) nucleosides are prepared.

9-(2'deoxy-2'-fluoro-β-D-arabinofuranosyl)purine,
9-(2'deoxy-2'-fluoro-β-D-arabinofuranosyl)thioguanine,
9-(2'deoxy-2'-fluoro-β-D-arabinofuranosyl)-N$^6$-trityladenine,
9-(2'deoxy-2'-fluoro-β-D-arabinofuranosyl)-N$^6$-acetyladenine,
9-(2'deoxy-2'-fluoro-β-D-arabinofuranosyl)-N$^6$-benzoyladenine,
9-(2'deoxy-2'-fluoro-β-D-arabinofuranosyl)hypoxanthine,
9-(2'deoxy-2'-fluoro-β-D-arabinofuranosyl)-guanine,
9-(2'deoxy-2'-fluoro-β-D-arabinofuranosyl)-N$^2$-acetylguanine,
9-(2'deoxy-2'-fluoro-β-D-arabinofuranosyl)-N$^2$-benzoylguanine,
9-(2'deoxy-2'-fluoro-β-D-arabinofuranosyl)-N$^2$-isobutyrylguanine,
9-(2'deoxy-2'-fluoro-β-D-arabinofuranosyl)-6-chloropurine,
9-(2'deoxy-2'-fluoro-β-D-arabinofuranosyl)-6-thiopurine,
9-(2'deoxy-2'-fluoro-β-D-arabinofuranosyl)-6-methylthiopurine,
9-(2'deoxy-2'-fluoro-β-D-arabinofuranosyl)-6-aminomethylpurine,
9-(2'deoxy-2'-fluoro-β-D-arabinofuranosyl)-6-dimethylaminopurine,
9-(2'deoxy-2'-fluoro-β-D-arabinofuranosyl)-2-aminopurine,
9-(2'deoxy-2'-fluoro-β-D-arabinofuranosyl)-2-acetamidopurine,
9-(2'deoxy-2'-fluoro-β-D-arabinofuranosyl)-2-benzamidopurine,
9-(2'deoxy-2'-fluoro-β-D-arabinofuranosyl)-2-isobytanamidopurine,
9-(2'deoxy-2'-fluoro-β-D-arabinofuranosyl)-2,6-diaminopurine,
9-(2'deoxy-2'-fluoro-β-D-arabinofuranosyl)-2,6-diacetamidopurine,
9-(2'deoxy-2'-fluoro-β-D-arabinofuranosyl)-2,6-dibenzamidopurine,
9-(2'deoxy-2'-fluoro-β-D-arabinofuranosyl)-2,6-diisobutanamidopurine,
9-(2'deoxy-2'-fluoro-β-D-arabinofuranosyl)-2-amino-6-chloropurine,
9-(2'deoxy-2'-fluoro-β-D-arabinofuranosyl)-2-amino-6-thiopurine,
9-(2'deoxy-2'-fluoro-β-D-arabinofuranosyl)-2-amino-6-methylthiopurine,
9-(2'deoxy-2'-fluoro-β-D-arabinofuranosyl)-2-fluoropurine,
9-(2'deoxy-2'-fluoro-β-D-arabinofuranosyl)-2-fluoroadenine,
9-(2'deoxy-2'-fluoro-β-D-arabinofuranosyl)-2-fluorohypoxanthine,
9-(2'deoxy-2'-fluoro-β-D-arabinofuranosyl)-2-fluoro-6-thiopurine,
9-(2'deoxy-2'-fluoro-β-D-arabinofuranosyl)-2-fluoro-6-methylthiopurine,
9-(2'deoxy-2'-fluoro-β-D-arabinofuranosyl)-2-fluoro-6-aminomethylpurine, and
9-(2'deoxy-2'-fluoro-β-D-arabinofuranosyl)-2-fluoro-6-dimethylaminopurine.

Discussion

The inhibitory activity of F-ara-H (9-2'-fluoro-2'-deoxy-β-D-arabinofuranosyl)-hypoxanthine against Leishmania tropica prompted the preparation of large amounts of this compound for more detailed biological evaluation. The only available method was the procedure used in U.S. Pat. Nos. 4,751,221 and 4,918,179, which was very inefficient.

The present inventive synthesis started from the readily available natural nucleoside, inosine, which was first protected at the 3' and 5' positions, and then the 2' hydroxy group was triflated followed by treatment with a fluorinating agent such as potassium fluoride, tetrabutylammonium fluoride, Amberlyst 26 (F$^-$ form) or tris(dimethylamino)-sulfur(trimethylsilyl)difluoride (TASF).

Acetyl, benzoyl, benzyl, tetahydropyranyl and silyl protecting groups were tested to protect the 3',5' positions. Such 3',5'-di-O-protected nucleosides were converted into their corresponding 2'-O-triflyl derivatives which were obtained generally in good yield. However, treatment of such 2'-O-triflyl nucleosides with potassium fluoride in dimethylformamide, tetrabutylammonium fluoride in dimethyl-formamide, Amberlyst 26 (F$^-$ form) in acetone or TASF in methylene chloride always produced a multi-component mixture from which 4,6-disubstituted furfuryl alcohol, 6-substituted 4-hydroxyfurfuryl alcohol, and purine base (products of elimination reaction) were isolated together with small amounts of untreated starting material and unfluorinated arabinosylpurine. Also treated were 3',5'-di-O-protected 2'unsubstituted purine nucleosides with diethylamino-sulfurtrifluoride (DAST). The reaction generally gave a mixture of many components from which the fluorinated product was isolated, after extremely laborious chromatographic separation, in only less than two percent yield at best.

It was found that unlike other 3'5'-di-O-protected derivatives, 5'-O-trityl nucleosides appeared to adapt the unusual $^2T_3$ (D) twist conformation as evidenced by a large H-1' and H-2' coupling ($J_{1',2'}$=6.3–7.2 Hz) in nuclear magnetic resonance spectroscopy. In this conformation, both the aglycon and 2'-O-triflyl group were in a quasi-equatorial disposition, which is not favorable for elimination reaction, leading to the formation of furfuryl alcohol derivatives. Also, the C2' position in this twisted conformation appeared to be least sterically hindered for the approach of the fluoride nucleophile. Indeed, after treatment of 5'-O-trityl-3'-O-acetyl-2'-O-triflyl-1-benzylinosine (see 2a, FIG. 1) with TASF, the desired 2'-"up"-fluorinated nucleoside (3a) was isolated in approximately 10% yield. Conversion of (3a) into F-ara-H proceeded very smoothly. The overall yield of F-ara-H by this procedure was several fold better than that of the original synthesis. Among several 5'-O-trityl-3'-protected-2'-O-triflyl-1-benzylinosine derivatives that were tested, the best result was obtained with 3',5'-di-O-trityl-2'-O-triflyl-1-benzylinosine (2b). When (2b) was treated with TASF, the desired fluorinated nucleoside (3b) was obtained in 30% yield. Again, deprotection of (3b) to F-ara-H occurred in high yield.

Treatment of 3',5'-di-O-trityl-1-benzylinosine (1b) with DAST afforded 60% yield of the fluorinated product (3b). Tri-O$^{3'}$, O$^{5'}$, N$^6$-trityladenosine, 3',5'-di-O-tritylinosine and 2-N-protected-3',5'-di-O-tritylguanosine also afforded their corresponding 2'-fluorinated arabinosyl nucleosides with somewhat lower yields.

What is claimed is:

1. A compound having the structure:

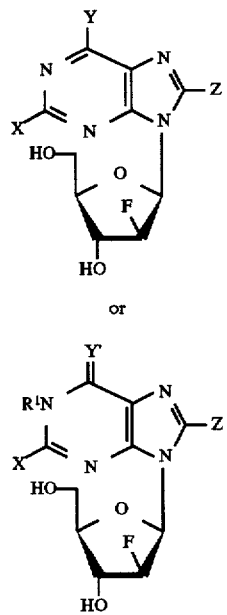

wherein in I, X is an amido or substituted amido group; and Z is hydrogen, or a hydroxyl, methoxy, or halogen group;

wherein in II, X is a fluoro group; and Z is hydrogen or a hydroxyl, methoxy, halogen, amino or substituted amino group;

R$^1$ is a benzyl or substituted benzyl group;

Y is hydrogen or a methylthio, benzylthio, isopropyl, amino, substituted amino or chloro group; and Y$^1$ is an oxo or thio group.

2. A compound of claim 1 selected from the group consisting of:

9-(2-deoxy-2-fluoro-β-D-arabinofuranosyl)-2-acetamidopurine, 9-(2-deoxy-2-fluoro-β-D-arabinofuranosyl)-2-benzamidopurine, 9-(2-deoxy-2-fluoro-β-D-arabinofuranosyl)-2-isobutanamidopurine 9-(2-deoxy-2-fluoro-β-D-arabinofuranosyl)-2,6-diacetamidopurine, 9-(2-deoxy-2-fluoro-β-D-arabinofuranosyl)-2,6-dibenzamidopurine, 9-(2-deoxy-2-fluoro-β-D-arabinofuranosyl)-2,6-diisobutanamidopurine, 9-(2-deoxy-2-fluoro-β-D-arabinofuranosyl)-2-fluoro-6-thiopurine, 9-(2-deoxy-2-fluoro-β-D-arabinofuranosyl)-2-acetamidoadenine, 9-(2-deoxy-2-fluoro-β-D-arabinofuranosyl)-2-benzamidoadenine, .

9-(2-deoxy-2-fluoro-β-D-arabinofuranosyl)-2-isobutanamidoadenine, or 9-(2-deoxy-2-fluoro-β-D-arabinofuranosyl)-2-fluorohypoxanthine.

3. A compound having the structure:

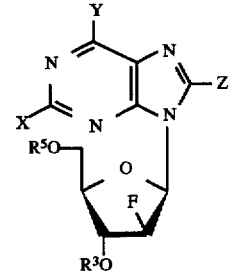

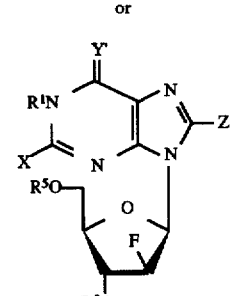

wherein in III, X is hydrogen, an amino or substituted amino group;

wherein in IV, X is hydrogen, a fluoro, amino or substituted amino group;

R$^5$ is triphenylmethyl, diphenyl(4-methoxyphenyl)methyl, or phenyldi(4-methoxyphenyl)methyl;

R$^3$ is hydrogen, triflyl, triphenylmethyl, diphenyl(4-methoxyphenyl)methyl, phenyldi(4-methoxyphenyl)methyl, tetrahydropyranyl, propanoyl, anisoyl, toluoyl, nitrobenzoyl, benzyl, toluyl, methoxybenzyl, or nitrobenzyl;

R¹ is hydrogen, or a benzyl or substituted benzyl group;

Y is hydrogen, or a methoxy, methylthio, benzylthio, isopropyl, chloro, amino or substituted amino group;

Y¹ is an oxo or thio group; and

Z is hydrogen, or a hydroxyl, methoxy, halogen, amino or substituted amino group.

4. A compound of claim 3 selected from the group consisting of:

9-(2-deoxy-2-fluoro-3,5-di-O-trityl-β-D-arabinofuranosyl) purine, 9-(2-deoxy-2-fluoro-3,5-di-O-trityl-β-D-arabinofuranosyl)-6-chloropurine, 9-(2-deoxy-2-fluoro-3,5-di-O-trityl-β-D-arabinofuranosyl)-6-thiopurine, 9-(2-deoxy-2-fluoro-3,5-di-O-trityl-β-D-arabinofuranosyl)-6-methylthiopurine, 9-(2-deoxy-2-fluoro-3,5-di-O-trityl-β-D-arabinofuranosyl)-6-aminomethylpurine, 9-(2-deoxy-2-fluoro-3,5-di-O-trityl-β-D-arabinofuranosyl)-6-dimethylaminopurine, 9-(2-deoxy-2-fluoro-3,5-di-O-trityl-β-D-arabinofuranosyl)-2-aminopurine, 9-(2-deoxy-2-fluoro-3,5-di-O-trityl-β-D-arabinofuranosyl)-2-benzamidopurine, 9-(2-deoxy-2-fluoro-3,5-di-O-trityl-β-D-arabinofuranosyl)-2-butanamidopurine, 9-(2-deoxy-2-fluoro-3,5-di-O-trityl-β-D-arabinofuranosyl)-2,6-diaminopurine, 9-(2-deoxy-2-fluoro-3,5-di-O-trityl-β-D-arabinofuranosyl)-2,6-diacetamidopurine, 9-(2-deoxy-2-fluoro-3,5-di-O-trityl-β-D-arabinofuranosyl)-2,6-dibenzamidopurine, 9-(2-deoxy-2-fluoro-3,5-di-O-trityl-β-D-arabinofuranosyl)-2,6-diisobutanamidopurine, 9-(2-deoxy-2-fluoro-3,5-di-O-trityl-β-D-arabinofuranosyl)-2-amino-6-chloropurine, 9-(2-deoxy-2-fluoro-3,5-di-O-trityl-β-D-arabinofuranosyl)-2-amino-6-thiopurine, 9-(2-deoxy-2-fluoro-3,5-di-O-trityl-β-D-arabinofuranosyl)-2-amino-6-methylthiopurine, 9-(2-deoxy-2-fluoro-3,5-di-O-trityl-β-D-arabinofuranosyl)-2-fluoro-6-thiopurine, 9-(2-deoxy-2-fluoro-3,5-di-O-trityl-β-D-arabinofuranosyl)-2-fluoro-6-methylthiopurine, 9-(2-deoxy-2-fluoro-3,5-di-O-trityl-β-D-arabinofuranosyl)-N⁶-trityladenine, 9-(2-deoxy-2-fluoro-3,5-di-O-trityl-β-D-arabinofuranosyl)-N⁶-acetyladenine, 9-(2-deoxy-2-fluoro-3,5-di-O-trityl-β-D-arabinofuranosyl)-N⁶-benzoyladenine, 9-(2-deoxy-2-fluoro-3,5-di-O-trityl-β-D-arabinofuranosyl)-2-fluorohypoxanthine, 9-(2-deoxy-2-fluoro-3,5-di-O-trityl-β-D-arabinofuranosyl)-hypoxanthine, 9-(2-deoxy-2-fluoro-3,5-di-O-trityl-β-D-arabinofuranosyl)-guanine, 9-(2-deoxy-2-fluoro-3,5-di-O-trityl-β-D-arabinofuranosyl)-N²-acetylguanine, 9-(2-deoxy-2-fluoro-3,5-di-O-trityl-β-D-arabinofuranosyl)-N²-benzoylguanine, 9-(2-deoxy-2-fluoro-3,5-di-O-trityl-β-D-arabinofuranosyl)-N²-isobutyrylguanine, 9-(2-deoxy-2-fluoro-3,5-di-O-trityl-β-D-arabinofuranosyl)-2-fluorohypoxanthine, or 9-(2-deoxy-2-fluoro-3,5-di-O-trityl-β-D-arabinofuranosyl)-6-acetamidopurine.

\* \* \* \* \*